US010398338B2

(12) United States Patent
Ghoraani et al.

(10) Patent No.: US 10,398,338 B2
(45) Date of Patent: Sep. 3, 2019

(54) SYSTEMS AND METHODS FOR GUIDING A MULTI-POLE SENSOR CATHETER TO LOCATE CARDIAC ARRHYTHMIA SOURCES

(71) Applicant: Florida Atlantic University Board of Trustees, Boca Raton, FL (US)

(72) Inventors: Behnaz Ghoraani, Boca Raton, FL (US); Prasanth Ganesan, Boca Raton, FL (US)

(73) Assignee: Florida Atlantic University Board of Trustees, Boca Raton, FL (US)

( * ) Notice: Subject to any disclaimer, the term of this patent is extended or adjusted under 35 U.S.C. 154(b) by 93 days.

(21) Appl. No.: 15/727,393

(22) Filed: Oct. 6, 2017

(65) Prior Publication Data

US 2019/0104962 A1 Apr. 11, 2019

(51) Int. Cl.
*A61B 5/00* (2006.01)
*A61B 5/0432* (2006.01)
*A61B 34/20* (2016.01)
*A61B 5/046* (2006.01)
*G16H 30/20* (2018.01)
(Continued)

(52) U.S. Cl.
CPC .......... *A61B 5/04325* (2013.01); *A61B 5/046* (2013.01); *A61B 5/6886* (2013.01); *A61B 5/725* (2013.01); *A61B 5/7282* (2013.01); *A61B 5/743* (2013.01); *A61B 34/20* (2016.02); *A61B 5/0422* (2013.01); *A61B 5/4836* (2013.01); *A61B 5/6858* (2013.01); *A61B 18/1206* (2013.01); *A61B 18/1492* (2013.01); *A61B 2017/00053* (2013.01); *A61B 2018/00351* (2013.01); *A61B 2018/00577* (2013.01);
(Continued)

(58) Field of Classification Search
CPC ... A61B 5/0432; A61B 5/04325; A61B 5/044; A61B 5/065–068; A61B 5/06; A61B 5/6844; A61B 5/6846; A61B 5/743
See application file for complete search history.

(56) References Cited

U.S. PATENT DOCUMENTS 5,741,214 A 4/1998 Ouchi et al.
6,226,542 B1 5/2001 Reisfeld
(Continued)

FOREIGN PATENT DOCUMENTS

WO 2013052944 A1 4/2013

OTHER PUBLICATIONS

International Search Report dated Dec. 4, 2018 in PCT/IB2018/055463.
International Search Report dated Aug. 24, 2018 in PCT/IB2018/053195.
(Continued)

*Primary Examiner* — Scott M. Getzow
(74) *Attorney, Agent, or Firm* — Fox Rothschild LLP

(57) ABSTRACT

Systems and methods for guiding a sensor to a location of a propagating wave source. The methods comprise: receiving, by the computing device, a plurality of signals generated by a plurality of electrodes of the sensor while the sensor resides at the first location in the object; processing, by the computing device, the plurality of signals to determine coordinates of an estimated location of the propagating wave source relative to the first location at which the sensor resides; and providing a visual aid facilitating sensor movement by plotting a dot on a grid overlaid on top of an object image displayed by the computing device.

22 Claims, 25 Drawing Sheets

(51) Int. Cl.
 A61B 5/042 (2006.01)
 A61B 18/12 (2006.01)
 A61B 18/14 (2006.01)
 A61B 17/00 (2006.01)
 A61B 18/00 (2006.01)

(52) U.S. Cl.
 CPC .............. *A61B 2018/00904* (2013.01); *A61B 2034/2055* (2016.02); *G16H 30/20* (2018.01)

(56) References Cited

U.S. PATENT DOCUMENTS

| | | |
|---|---|---|
| 7,263,397 B2 | 8/2007 | Hauck et al. |
| 2007/0021679 A1 | 1/2007 | Narayan et al. |
| 2013/0116538 A1 | 5/2013 | Herzog et al. |
| 2013/0116681 A1 | 5/2013 | Zhang |
| 2013/0274582 A1 | 10/2013 | Afonso et al. |
| 2014/0081114 A1 | 3/2014 | Shachar et al. |
| 2015/0164356 A1 | 6/2015 | Merschon et al. |
| 2015/0208942 A1 | 7/2015 | Bar-Tal et al. |
| 2015/0289807 A1 | 10/2015 | Narayan et al. |
| 2015/0327805 A1 | 11/2015 | Ben-Haim |
| 2016/0010077 A1 | 1/2016 | Urban et al. |
| 2016/0100770 A1 | 4/2016 | Afonso et al. |
| 2016/0183824 A1 | 6/2016 | Severino |
| 2016/0183830 A1 | 6/2016 | Laughner et al. |
| 2016/0331337 A1 | 11/2016 | Ben-Haim |
| 2017/0008669 A1 | 1/2017 | Stahl |
| 2017/0020247 A1 | 1/2017 | Petrosyan |
| 2017/0028103 A1 | 2/2017 | Song et al. |
| 2017/0033297 A1 | 2/2017 | Park et al. |
| 2017/0086694 A1 | 3/2017 | Stewart et al. |
| 2017/0202472 A1 | 7/2017 | Zeidan et al. |
| 2017/0281031 A1 | 10/2017 | Houben et al. |
| 2017/0304644 A1* | 10/2017 | Kruecker .............. A61B 90/37 |
| 2017/0332971 A1 | 11/2017 | Macneil et al. |

OTHER PUBLICATIONS

Narayan, S.M., et al., "Clinical Mapping Approach to Diagnose Electrical Rotors and Focal Impulse Sources for Human °dna! Fibrillation," Journal of Cardiovascular Electrophysiology, vol. 23, Issue 5, May 2012, ISSN: 1045-3873.

Narayan, S.M., et al., "Ablation of Rotor and Focal Sources Reduces Late Recurrence of Atrial Fibrillation Compared to Trigge Ablation Alone," Journal of the American College of Cardiology (2014), doi: 10/1016j.jacc.2014.02.543.

Ganesan, P., et al., "Characterization of Electrograms from Multi-polar Diagnostic Catheters During Atrial Fibrillation,"—Iindawi Publishing Corporation, BioMed Research International, vol. 2015, Article ID 272954, copyright 2015.

Salmin, A.J., et al., A Novel Catheter-Guidance Algorithm for Localization of Atrial Fibrillation Rotor and Focal Sources, copyright 2016 IEEE, 978-1-4577-0220-4/16.

Salmin, A.J., et al., "An Algorithm to Guide Multi-Pole Diagnostic Catheters Towards an Atrial Fibrillation Sustaining Site," Rochester Institute of Technology, SUNY Upstate Medical University, Nov. 2015.

Salmin, A., et al., "An Algorithm to Guide Multi-Pole Diagnostic Catheters Towards an Atrial Fibrillation Sustaining Site," Rochester Institute of Technology, SUNY Upstate Medical University, Jan. 2016.

Salmin, A.J., et al., "Developing and Evaluating a Novel Tracking Algorithm to Guide Multi-Pole Diagnostic Catheters Towards Atrial Fibrillation Sites," University of Rochester Medical Center, UPSTATE Medical University, May 2016.

Ganesan, P , et al., "Development of a Novel Probabilistic Algorithm for Localization of Rotors during Atrial Fibrillation," copyright 2016 IEEE, 978-1-4577-0220-4/16.

Ganesan, P et al., "Rotational Activities During Atrial Fibrillation Assocaite with Incremental Gradient of Total of Technology, SUNY Upstate Medical, Sonduction Delay from Multi-Polar Diagnostic Catheters," Rochester Institute University, BSIA Lab, Oct. 2014.

* cited by examiner

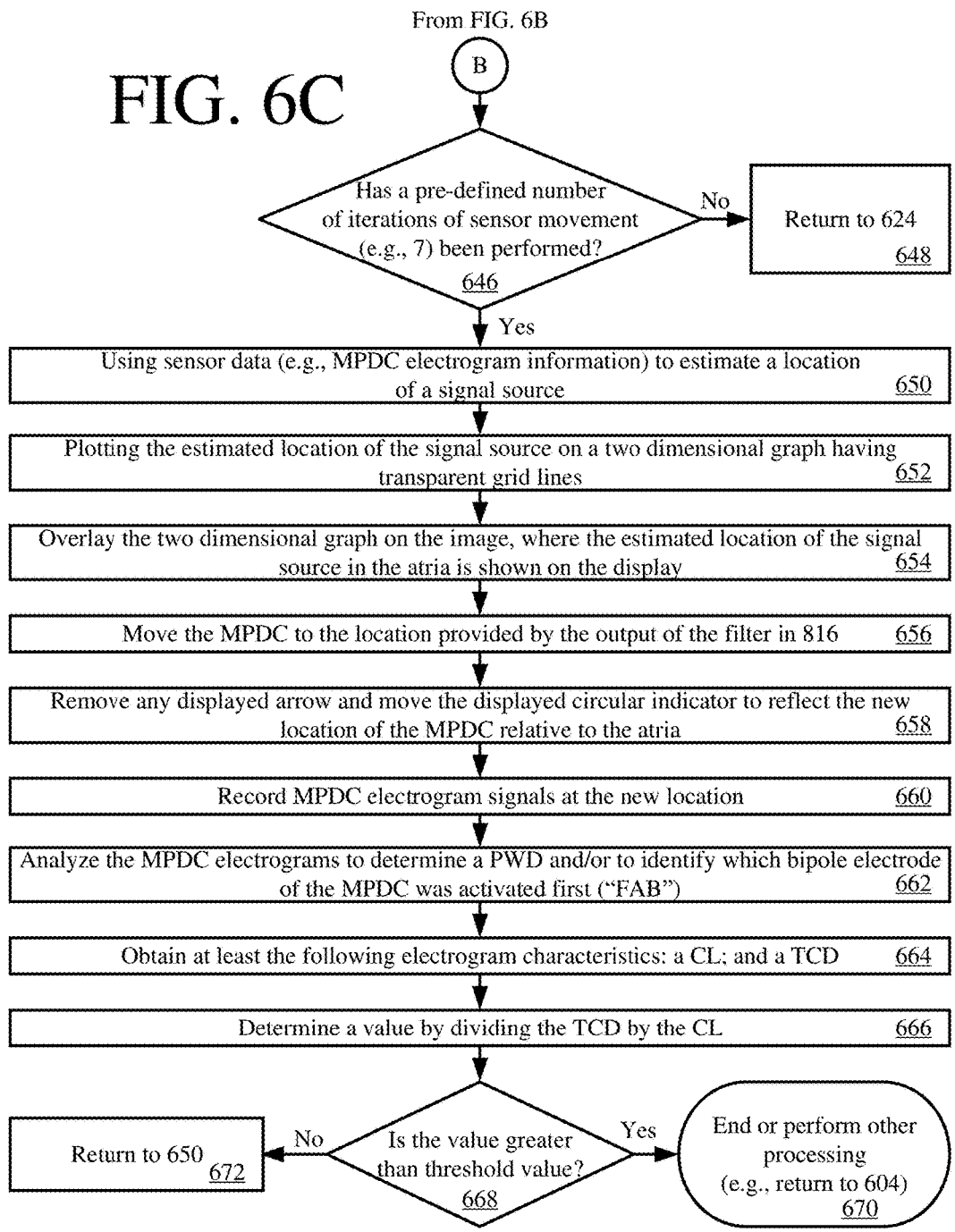

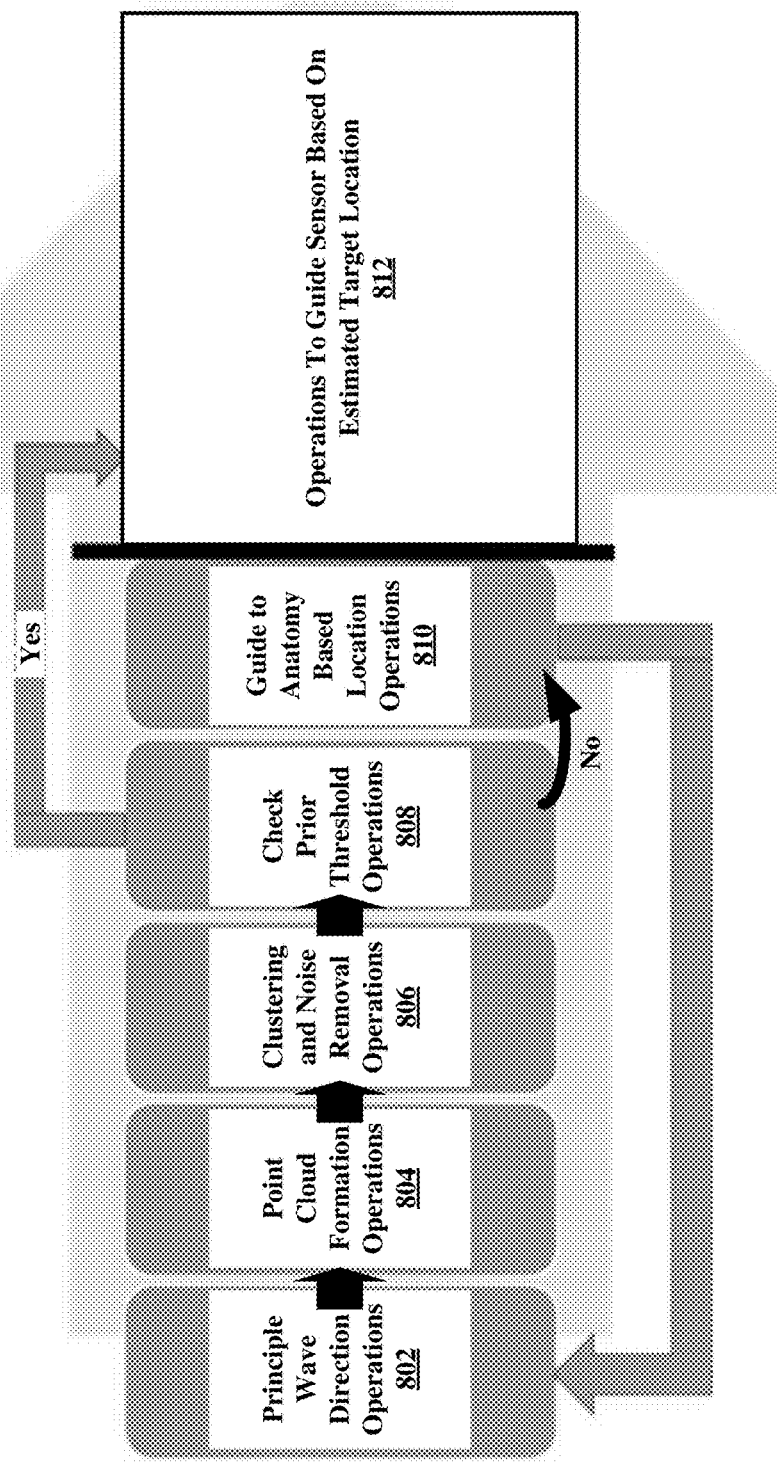

Operations To Guide Sensor Based On Estimated Target Location 812

Estimate Target Observation Operations 814

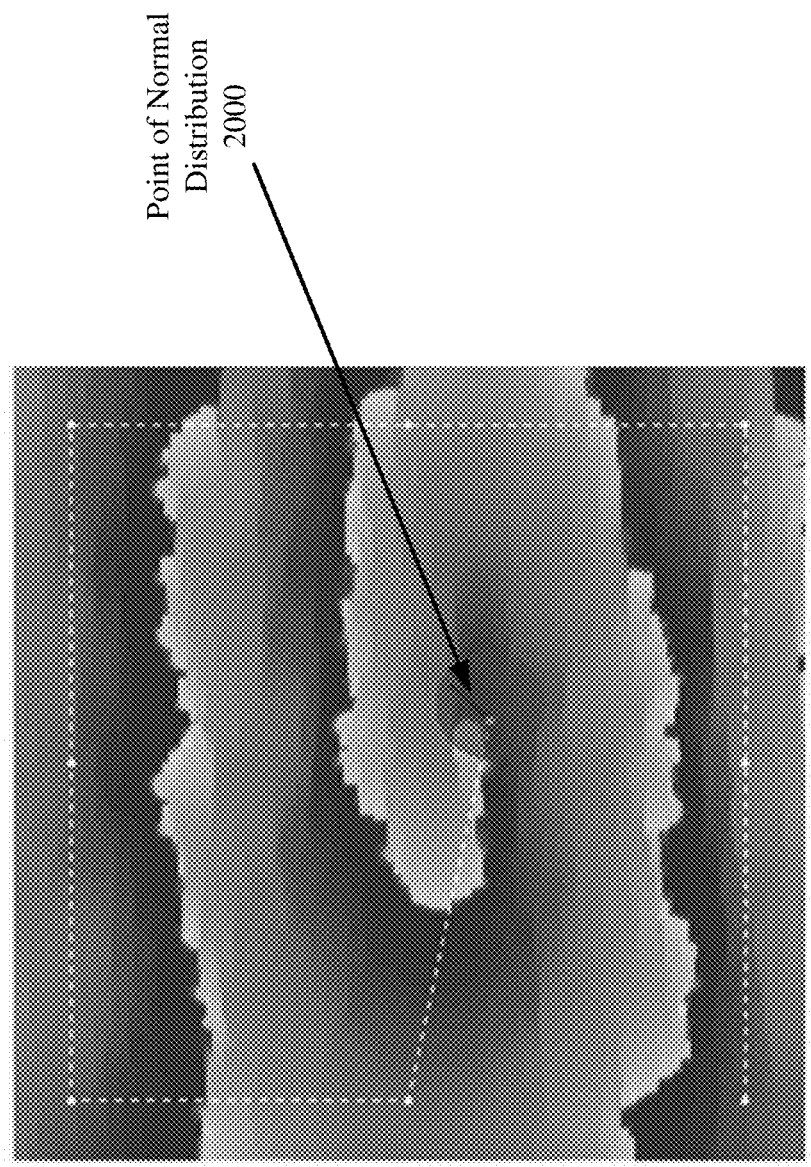

SYSTEMS AND METHODS FOR GUIDING A MULTI-POLE SENSOR CATHETER TO LOCATE CARDIAC ARRHYTHMIA SOURCES

STATEMENT REGARDING FEDERAL FUNDING

This invention was made with government support under contract number R15 HL127663 awarded by the National Institute of Health. The government has certain rights in the invention.

BACKGROUND

Statement of the Technical Field

The present disclosure concerns generally to computing devices. More particularly, the present invention relates to implementing systems and methods for guiding a multi-pole sensor catheter to locate cardiac arrhythmia sources.

Description of the Related Art

Atrial Fibrillation ("AF") is the most common heart rhythm disorder and affects 2.7 million Americans, accounting for frequent health care utilization, increased hospitalizations and increased risks of stroke, heart failure and mortality. Ectopic beats from the pulmonary veins may trigger AF, the discovery of which led to the development of a non-pharmacological ablation therapy called Pulmonary Vein ("PV") isolation, which uses radiofrequency energy to cauterize the atrial tissue in the PV's antrum in order to terminate AF and restore sinus rhythm. Unfortunately, this therapy remains suboptimal with long-term success rates of only 40% to 60%. One of the main reasons for such unsuccessful outcomes is that it fails to eliminate AF drivers outside the PVs, and their targeted elimination is key to improving outcome after AF ablation. Detection and ablation of the rotors or foci has a very significant impact on the successful termination of AF. In animal studies where AF is induced with acetylcholine and rapid pacing, optical phase mapping of action potentials has shown that rotors outside PVs are relevant to the perpetuation of AF and should be targeted for AF ablation. Similarly, in human studies, phase maps derived from basket catheter unipolar electrograms have been used to detect rotors and foci and ablate these sites. It has been shown that ablation of rotor AF sources along with PV isolation is more durable than standalone PV isolation at preventing AF recurrence at 3 year-follow up.

However, a recent method to location rotors is based on a 64-pole basket catheter and inherits the limitations of a basket catheter. For example, the resolution is limited to the proportion of electrodes in contact with endocardium and good electrode contact at all sites on the endocardium is difficult to ensure because of irregularities in the cardiac chamber surface, so that areas crucial to the arrhythmia circuit may not be recorded. Moreover, regions such as the left atrial appendage are incompletely covered by the basket catheter. As a result, the basket catheter does not record arrhythmia substrates involving these structures. Additionally, basket catheter mapping does not permit immediate correlation of activation times to precise anatomical sites, and a Multi-Polar Diagnostic Catheter ("MPDC") must still be manipulated to the identified site for more precise mapping and localization of the target for ablation, as well as for RF energy delivery. Basket catheters also have limited torque capabilities and limited maneuverability, which hamper correct placement, and they can abrade the endocardium.

SUMMARY

The present invention concerns implementing systems and methods for guiding a sensor (e.g., a multi-pole sensor catheter) to a location of a propagating wave source. The method comprising: receiving, by the computing device, a plurality of signals generated by a plurality of electrodes of the sensor while the sensor resides at the first location in the object; processing, by the computing device, the plurality of signals to determine coordinates of an estimated location of the propagating wave source relative to the first location at which the sensor resides; and providing a visual aid facilitating sensor movement by plotting a dot on a grid overlaid on top of an object image displayed by the computing device.

In some scenarios, the methods further comprise guiding the sensor movement to a second location in the object based on an anatomy until a pre-defined criteria is met. The pre-defined criteria comprises at least one of a number of iterations performed and a number of points in a cluster.

In those or other scenarios, the processing comprises: using the plurality of signals to determine a Principle Wave Direction ("PWD") to the propagating wave source; and using the PWD to determine if there are enough points to generate a point cloud. If it is determined that there are not enough points to generate a point cloud, the sensor is guided to a next location in the object based on an anatomy. If it is determined that there are enough points to generate the point cloud, the point cloud is generated. The points of the point cloud are grouped into at least one cluster. The point cloud and the at least one cluster are used to determine coordinates of the dot. More particularly, the coordinates are determined by: identifying a cluster with a maximum density; determining a weighted average of the identified cluster's points; and performing a Bayesian filter algorithm using the weighted average to determine a next location in the object to where the sensor should be moved.

In those or yet other scenarios, operations are stopped when a stop condition is met. The stop condition is based on at least one of a Total Conduction Delay ("TCD") divided by a Cycle Length ("CL"), a Cycle Width ("CW") divided by CL, TCD/CW, characteristics of pattern of sensor movement, the source's distance from a current sensor location, and a source's distance from a previous sensor location. The stop condition is selected based on at least one of an amplitude of the plurality of signals and a target type.

BRIEF DESCRIPTION OF THE DRAWINGS

Embodiments will be described with reference to the following drawing figures, in which like numerals represent like items throughout the figures.

FIGS. 6(a)-6(c) (collectively referred to herein as "FIG. 6") provide a flow diagram of an exemplary method for localizing propagating wave sources using multi-pole sensors.

FIGS. 8A-8B (collectively referred to herein as "FIG. 8") provides an illustration that is useful for understanding a process for guiding a multi-pole sensor catheter to locate cardiac arrhythmia sources.

FIG. 20 provides an illustration that is useful for understanding map building operations of FIGS. 8 and 19.

DETAILED DESCRIPTION

Figure 1:
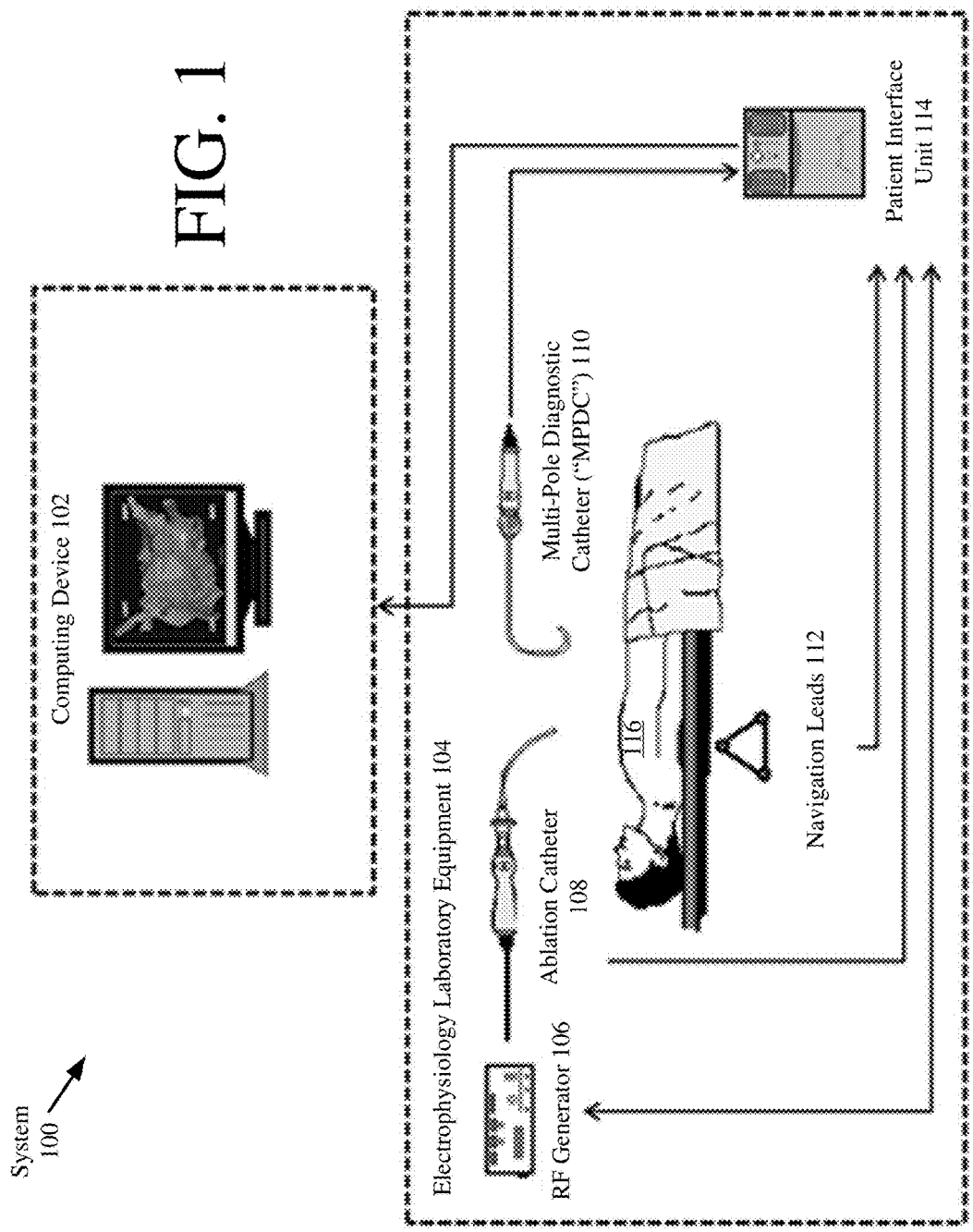
FIG. 1 is an illustration of an exemplary system.

It will be readily understood that the components of the embodiments as generally described herein and illustrated in the appended figures could be arranged and designed in a wide variety of different configurations. Thus, the following more detailed description of various embodiments, as represented in the figures, is not intended to limit the scope of the present disclosure, but is merely representative of various embodiments. While the various aspects of the embodiments are presented in drawings, the drawings are not necessarily drawn to scale unless specifically indicated.

The present invention may be embodied in other specific forms without departing from its spirit or essential characteristics. The described embodiments are to be considered in all respects only as illustrative and not restrictive. The scope of the invention is, therefore, indicated by the appended claims rather than by this detailed description. All changes which come within the meaning and range of equivalency of the claims are to be embraced within their scope.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussions of the features and advantages, and similar language, throughout the specification may, but do not necessarily, refer to the same embodiment.

Furthermore, the described features, advantages and characteristics of the invention may be combined in any suitable manner in one or more embodiments. One skilled in the relevant art will recognize, in light of the description herein, that the invention can be practiced without one or more of the specific features or advantages of a particular embodiment. In other instances, additional features and advantages may be recognized in certain embodiments that may not be present in all embodiments of the invention.

Reference throughout this specification to "one embodiment", "an embodiment", or similar language means that a particular feature, structure, or characteristic described in connection with the indicated embodiment is included in at least one embodiment of the present invention. Thus, the phrases "in one embodiment", "in an embodiment", and similar language throughout this specification may, but do not necessarily, all refer to the same embodiment.

As used in this document, the singular form "a", "an", and "the" include plural references unless the context clearly dictates otherwise. Unless defined otherwise, all technical and scientific terms used herein have the same meanings as commonly understood by one of ordinary skill in the art. As used in this document, the term "comprising" means "including, but not limited to".

The present document generally concerns systems and methods for guiding an MPDC in an object (e.g., the atria of a subject) or space to locate a cardiac arrhythmia source in the object or space. The present solution can be used in many applications. For example, the present solution can be used during an AF ablation procedure for successful detection and ablation of the AF sources (e.g., rotors or foci) outside the PVs and increasing the success of AF elimination procedures. The AF sources are sites with short cycle length, high dominant frequency, and/or high recurrence or similarity. Such AF sources include foci, rotors (spiral waves—meandering and non-meandering), scroll waves, and other arrhythmic source (e.g., AF, Atrial Tachycardia, Atrial Flutter, Ventricular Fibrillation, and/or Ventricular Tachycardia) this is in the form of a periodically/stably propagating wave without chaos. The present solution can be implemented in a computing device via hardware and/or software. In some scenarios, the present solution is implemented as a software add-on to the 3D mapping system in any of the existing AF mapping systems. Notably, the present solution is described below in relation to such an AF ablation procedure based scenario. However, the present solution is not limited in this regard. The present solution can be used in any application in which the source of a propagating wave of interest is to be located through an iterative process.

Referring now to FIG. 1, there is provided an illustration of an exemplary system 100. System 100 is entirely or at least partially disposed within a facility, such as an electrophysiology laboratory. System 100 comprises a computing device 102 and electrophysiology laboratory equipment 104. The computing device 102 is configured to receive sensor information from the electrophysiology laboratory equipment 104. The sensor information can be acquired using a patient interface unit 114 and an MPDC 110. The ablation is performed using RF generator 106 and an ablation catheter 108. Each of the listed devices 106-110 is well known in the art, and therefore will not be described in detail herein. Any known or to be known RF generator, ablation catheter and/or MPDC can be used herein without limitation. The sensor information is communicated from the electrophysiology laboratory equipment 104 to the computing device 102 via a patient interface unit 114. The patient interface unit 114 performs any required processing necessary to allow the computing device 102 and laboratory equipment 114 to interoperate and communicate information therebetween.

The present solution is not limited to the hardware shown in FIG. 1. For example, any multi-polar catheter with reasonable resolution (electrode spacing) can be used without limitation. Such multi-polar catheters include, but are not limited to, a circular catheter, a catheter with branches, a spiral catheter, and/or an array catheter.

Figure 2:
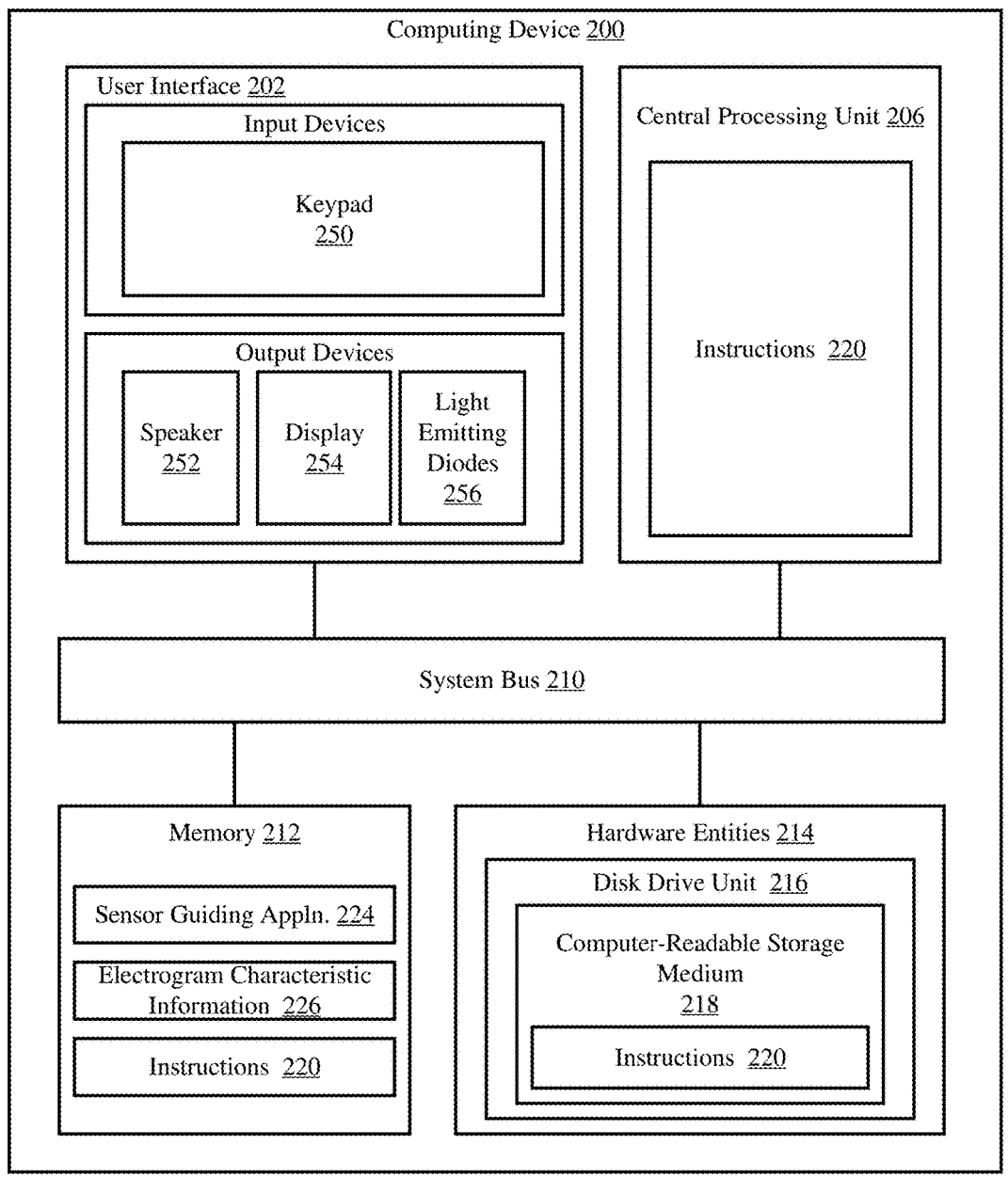
FIG. 2 is an illustration of an exemplary computing device.

Referring now to FIG. 2, there is provided a detailed block diagram of an exemplary architecture for a computing device 200. Computing device 102 of FIG. 1 is the same as or substantially similar to computing device 200. As such, the following discussion of computing device 200 is sufficient for understanding computing device 102.

Computing device 200 may include more or less components than those shown in FIG. 2. However, the components shown are sufficient to disclose an illustrative embodiment implementing the present solution. The hardware architecture of FIG. 2 represents one embodiment of a representative computing device configured to facilitate improved MPDC control and use. As such, the computing device 200 of FIG. 2 implements at least a portion of a method for automatically and dynamically guiding a sensing device (e.g., MPDC 110 of FIG. 1) to locate a signal source (e.g., a cardiac arrhythmia source or an AF source) in accordance with the present solution.

Some or all the components of the computing device 200 can be implemented as hardware, software and/or a combination of hardware and software. The hardware includes, but is not limited to, one or more electronic circuits. The electronic circuits can include, but are not limited to, passive components (e.g., resistors and capacitors) and/or active components (e.g., amplifiers and/or microprocessors). The passive and/or active components can be adapted to, arranged to and/or programmed to perform one or more of the methodologies, procedures, or functions described herein.

As shown in FIG. 2, the computing device 200 comprises a user interface 202, a Central Processing Unit ("CPU") 206, a system bus 210, a memory 212 connected to and accessible by other portions of computing device 200 through system bus 210, and hardware entities 214 connected to system bus 210. The user interface can include input devices (e.g., a keypad 250) and output devices (e.g., speaker 252, a display 254, and/or light emitting diodes 256), which facilitate user-software interactions for controlling operations of the computing device 200.

At least some of the hardware entities 214 perform actions involving access to and use of memory 212, which can be a RAM, a disk driver and/or a Compact Disc Read Only Memory ("CD-ROM"). Hardware entities 214 can include a disk drive unit 216 comprising a computer-readable storage medium 218 on which is stored one or more sets of instructions 220 (e.g., software code) configured to implement one or more of the methodologies, procedures, or functions described herein. The instructions 220 can also reside, completely or at least partially, within the memory 212 and/or within the CPU 206 during execution thereof by the computing device 200. The memory 212 and the CPU 206 also can constitute machine-readable media. The term "machine-readable media", as used here, refers to a single medium or multiple media (e.g., a centralized or distributed database, and/or associated caches and servers) that store the one or more sets of instructions 220. The term "machine-readable media", as used here, also refers to any medium that is capable of storing, encoding or carrying a set of instructions 220 for execution by the computing device 200 and that cause the computing device 200 to perform any one or more of the methodologies of the present disclosure.

In some scenarios, the hardware entities 214 include an electronic circuit (e.g., a processor) programmed for facilitating the provision of a target map showing the location of a propagating wave source (e.g., a cardiac arrhythmia source). In this regard, it should be understood that the electronic circuit can access and run a sensor guiding application 224 installed on the computing device 200. The software application 224 is generally operative to: use a known first location of the sensor in a space and known anatomy information to generate a target map to be overlayed on top of an image of an object or space in which the sensor is disposed; presenting the target map on a display screen for purposes of guiding movement of the sensor to a second location; iteratively updating the target map for purposes of guiding movement of the sensor to next third locations; obtaining stored electrogram sensor data acquired by the electrodes of the sensor located at the first, second and third locations in the space; determine electrogram characteristics using the electrogram sensor data; storing electrogram characteristic information 226 in memory 212; performing Bayesian filter operations using the electrogram characteristic information 226 to determine a likely location of a cardiac arrhythmia source in the object or space; and update the target map to include an indicator indicating the previously determined likely location of the cardiac arrhythmia source relative to the sensor's current location. The indicator may include, but is not limited to, a colored geometric shaped object (e.g., a circle, square, triangle, star, etc). The color of the indicator may be selected to show an amount of confidence that the etermined likely location of the cardiac arrhythmia source is accurate. Some or all of this process can be iteratively performed until certain stop conditions are met (e.g., when a TCD divided by a CL exceeds 0.7 and/or a confidence value exceeds a threshold value). Other functions of the software application 224 will become apparent as the discussion progresses.

The electrogram characteristic information 226 can specify at least one electrogram characteristic and/or include data that is useful for computing at least one electrogram characteristic. The electrogram characteristic can include, but is not limited to, a voltage, a PWD to a propagating wave source, a First Activated Bipole ("FAB"), a TCD, a CL, and/or other time domain characteristic obtained from unipolar or bipolar electrogram signals recorded by an MPDC (e.g., last activated bipole, cycle width, etc.).

The electrogram characteristic information 226 can be acquired automatically, manually, or semi-automatically. In the automatic scenarios, an automated algorithm is employed to detect the cycles and calculate the electrogram characteristics. In the manual scenarios, a clinician may manually/visually find the electrogram characteristics and input them into the system via user-software interactions. The user-software interactions can involve indicating an electrogram characteristic on an electrogram plot and/or inputting electrogram characteristic values directly. In the semi-automatic scenarios, a combined manual and automatic algorithm is employed. For example, the clinician manually indicates the cycles on the electrogram plot using a virtual pen. The rest of the tasks (e.g., computation of the electrogram characteristics) can be performed automatically by using the cycles indicated by the clinician.

Notably, the electrogram characteristics are converted to meaningful information by the computing device 102. Hence, any other forms of input that can be converted to the required information, or an input of the required information itself directly can be considered within the scope of the present solution. For example, the FAB characteristic is converted to the direction of the wave by the computing device 102. Hence, any other input that can be converted to the wave direction can be used herein without limitation. TCD and CL are used herein as a convergence condition. Hence, any other input or algorithm that allows one to check for convergence (i.e., whether the current MPDC location is an AF source or not) can be used herein without limitation.

As noted above, the electrogram characteristic information 226 can include, but is not limited to, a CL, a PWD, an FAB, and a TCD. CL, PWD, FAB and TCD are well known in the art, and therefore will not be described in detail herein. Still, a brief discussion of how these electrogram characteristics can be computed using an MPDC is now provided simply to assist the reader in fully understanding the present solution.

Figure 3:
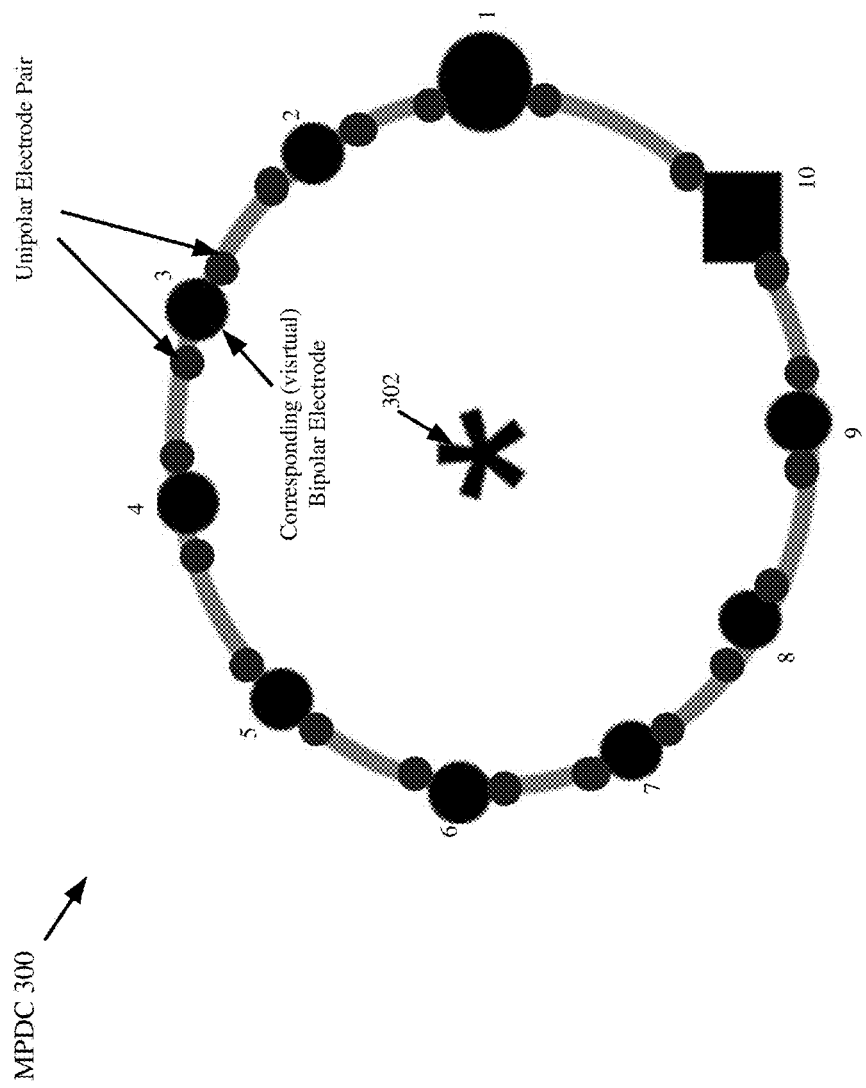
FIG. 3 provides an illustration of an exemplary electrode configuration for an MPDC in the system.

In order to understand how the electrogram characteristics are determined, an exemplary electrode configuration for an MPDC (e.g., MPDC 110 of FIG. 1) is explained with reference to FIG. 3. As shown in FIG. 3, a circular MPDC 300 comprises twenty (20) unipole electrodes that are arranged as pairs in a circular pattern such that the pairs are equally spaced for each other. Ten (10) bipole electrodes 1-10 are defined as mid-point positions of the unipole pairs as shown in FIG. 3 and equidistant from a center 302 of the MPDC. The electrogram signals generated by the unipole electrodes and/or bipole electrodes can be used herein to guide a sensor to locate a source of a propagating wave.

The present solution is not limited to the MPDC architecture shown in FIG. 3. Other types of MPDCs can be used herein. The other types of MPDCs include, but are not limited to, pentaray catheters and basket catheters.

Figure 4:
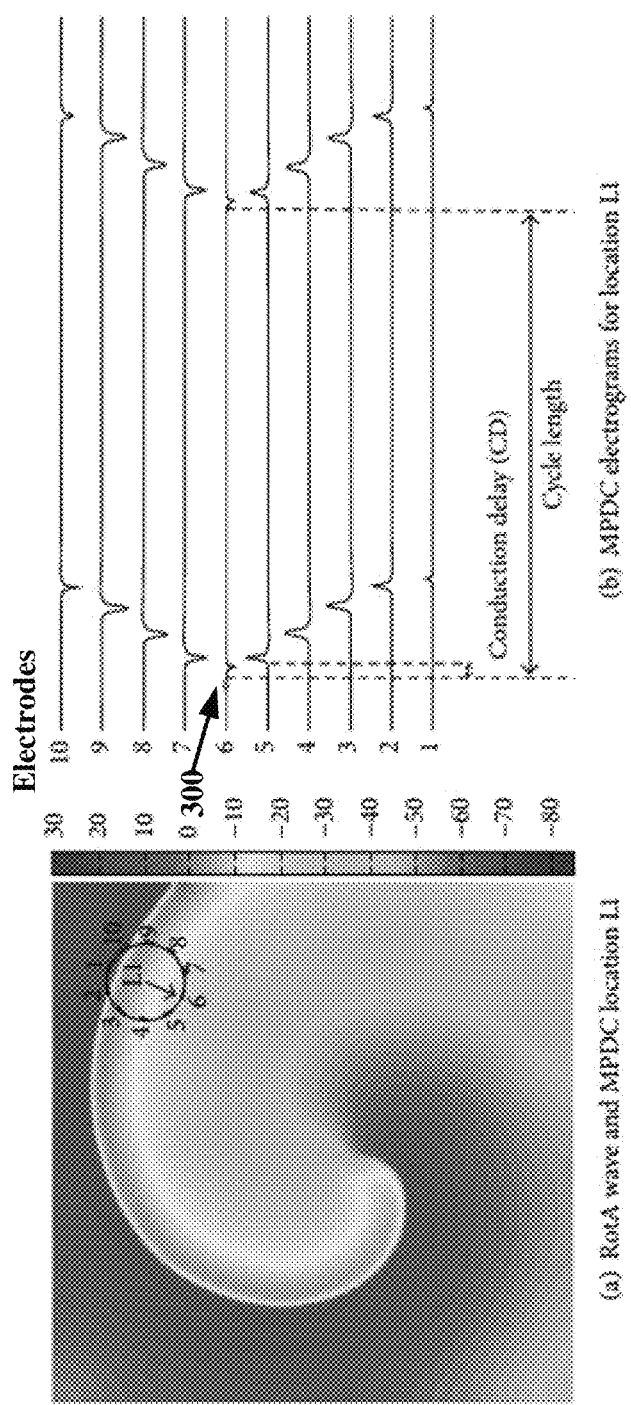
FIG. 4 provides graphs that are useful for understanding how electrogram characteristics can be determined based on electrogram sensor data acquired by electrodes of an MPDC.

Referring now to FIG. 4, there is provided graphs that are useful for understanding how electrogram characteristics can be determined based on electrogram sensor data acquired by the ten (10) bipole electrodes 1-10 of an MPDC (e.g., MPDC 110 of FIG. 1). The following electrogram characteristics can be determined at each recording site: PWD; FAB; TCD; and average CL at the FAB.

Figure 9:
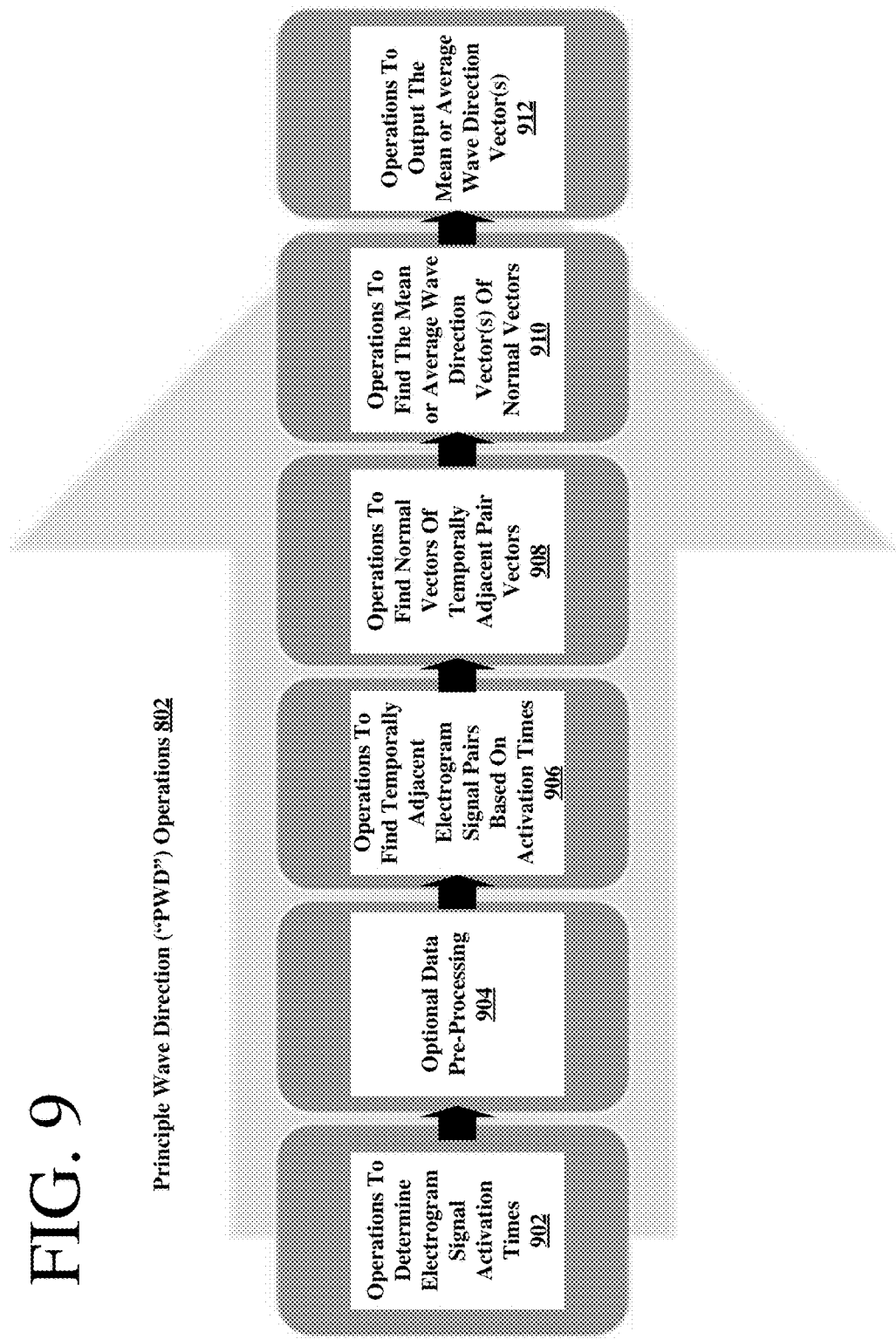
FIG. 9 provides an illustration that is useful for understanding Principle Wave Direction ("PWD") operations of FIG. 8.

PWD is generally an estimated direction to at least one propagating wave source relative to the sensor's current location. Techniques for determining a PWD are described in detail below in relation to FIGS. 9-10. As shown in FIG. 9, the PWD can be expressed as a mean or average wave direction vector.

The FAB also specifies an estimated direction to a propagating wave source. As such, the FAB can be used alternatively to the PWD. FAB is determined as the first bipole that encounters the wavefront (i.e., the bipole with the earliest Activation Time ("AT")). The AT of each bipole is calculated with respect to the beginning of the recordings. For example, in FIG. 4(*b*), the FAB 300 implies that at MPDC location L1 the earliest activation occurred at bipole electrode 6 of the MPDC. The FAB is shown as the head of the arrow in FIG. 4(*a*).

The CD of a particular bipole electrode is calculated as the interval from each local activation to that of the next bipole electrode. For example, in FIG. 4(*b*), the CD of bipole electrode 5 ($CD_5$) is calculated as the time interval between the activations of bipole electrode 6 and bipole electrode 5. The CD of bipole electrode 4 ($CD_4$) is calculated with respect to bipole 5, and so forth. The $CD_1$ through $CD_9$ computations are obtained in accordance with the following Mathematical Equation (1).

$$CD_i = AT_{i+1} - AT_i \quad (1)$$

Additionally, the CD of bipole electrode 10 ($CD_{10}$) is calculated as the time interval between bipole electrode 1 and bipole electrode 10 in accordance with the following Mathematical Equation (2).

$$CD_{10} = AT_1 - AT_{10} \quad (2)$$

Figure 5:
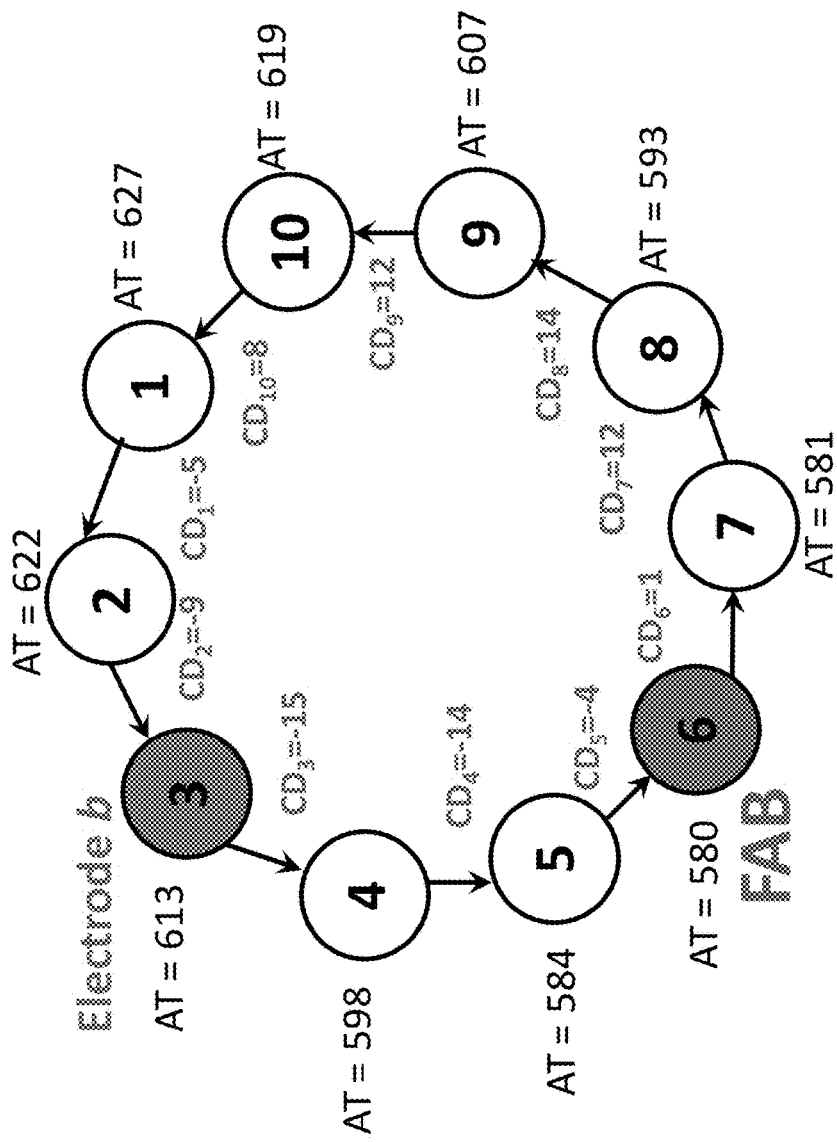
FIG. 5 provides a diagram that illustrates electrogram characteristics for an MPDC.

FIG. 5 illustrates how the CD and TCD calculations are performed for the MPDC in FIG. 4(*b*). Bipole electrode 6 is the FAB with the earliest activated time of 580 ms. $CD_1$ to $CD_{10}$ are calculated as explained above and shown for each bipole electrode. This procedure is continued for all cycles of the electrogram and the CD for every bipole electrode is averaged over the number of cycles to obtain a single value of CD for each electrode 1-10. Next, the electrode, b, with maximum absolute value CD was identified with the following Mathematical Equation (3)

$$b = \mathrm{argmax}(\{|CD_i|\}_{i=1:10}) \quad (3)$$

In FIG. 4(*b*), b is electrode 3 with the largest absolute value CD. Finally, the summation of the average CD of every electrode is calculated to obtain the TCD at each recording site. The mathematical expression for TCD at any MPDC location (e.g., L1) is given by the following Mathematical Equation (4)

$$TCD = |\Sigma_{i=1}^{10} CD_i - CD_b| \quad (4)$$

The CL is the time delay between two (2) successive activations in the same bipole electrode during consecutive cycles AT=607 (FIG. 3(*b*)). Here, CL is calculated as the average of the CL's for all of the bipole electrodes for a given MPDC location (e.g., L1). The CL of the FAB is calculated for different cycles and averaged over the number of cycles to obtain an average CL for the FAB.

Referring now to FIG. 6, there is provided a flow diagram of an exemplary method 600 for guiding an MPDC via a generated target map. Notably, method 600 is described in relation to an atria based scenario. Method 600 is not limited in this regard, and can be used in any application where a target is to be localized using sensors. A person skilled in the art would readily understand how method 600 can be modified for other applications.

Figure 6A:
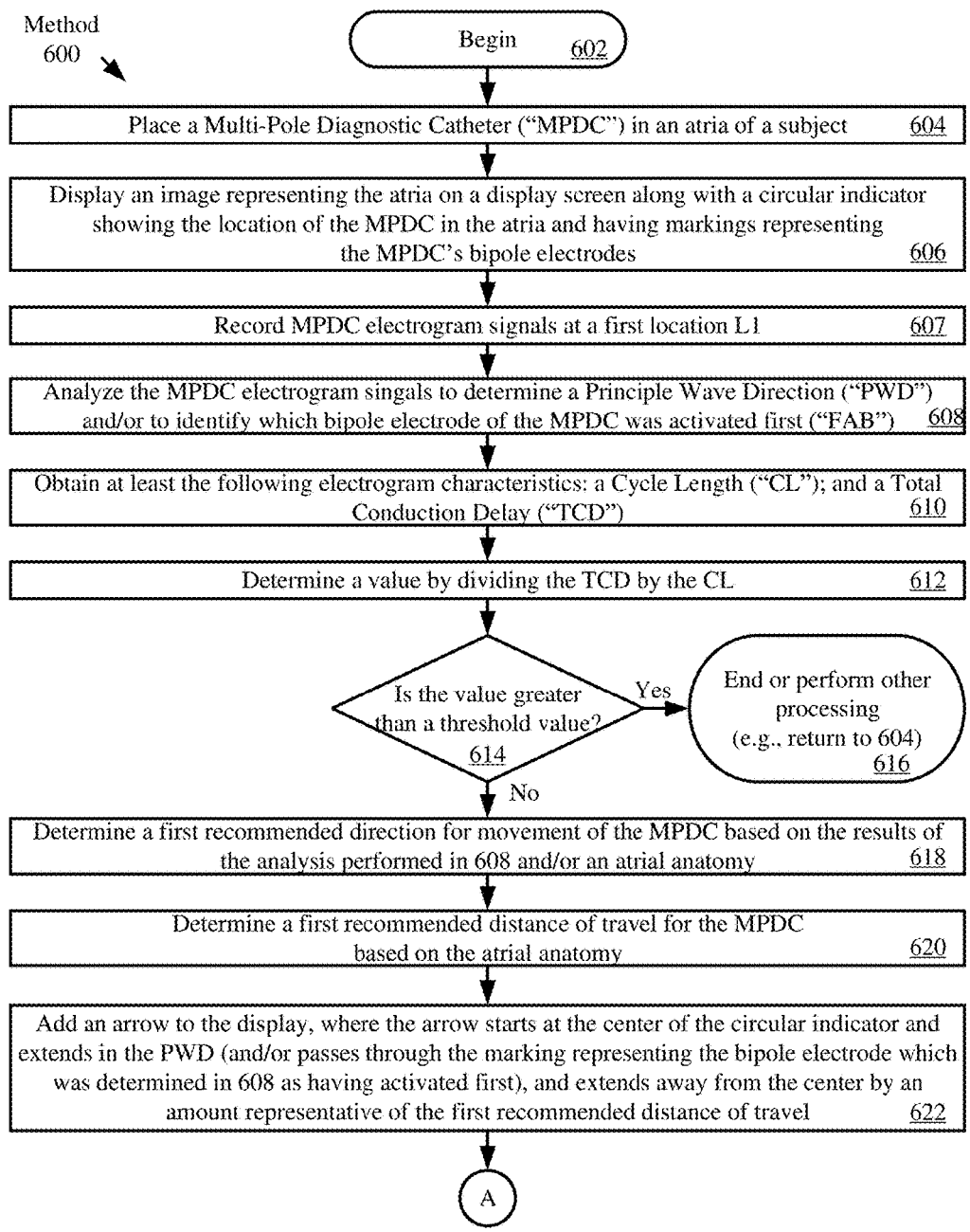

As shown in FIG. 6A, method 600 begins with 602 and continues with 604 where an MPDC (e.g., MPDC 110 of FIG. 1) is placed in an atria of a subject (e.g., person 116 of FIG. 1). Next in 606, an image representing the atria (or a portion of the atria) is displayed on a display screen (e.g., display 254 of FIG. 2) of a computing device (e.g., computing device 102 of FIG. 1 and/or 200 of FIG. 2) along with a circular indicator showing the first location L1 of the MPDC in the atria. The circular indicator comprises a plurality of markings representing the MPDC's bipole electrodes. An exemplary sensed image 700 of human tissue showing a sensed rotor is provided in FIG. 7(*a*). FIG. 7(*a*) also shows an exemplary circular indicator 702 comprising a plurality of markings 704.

MPDC electrogram signals are recorded in 607 while the MPDC is at the first location L1. An illustration of ten (10) raw bipolar electrogram signals is provided in FIG. 7(*b*). Techniques for recording MPDC electrogram signals are well known in the art, and therefore will not be described herein. Any known or to be known technique for recording MPDC electrogram signals can be used herein without limitation. In some scenarios, this recording is achieved by communicating electrogram information (or data) to the computing device for subsequently processing during method 600.

Figure 7A:
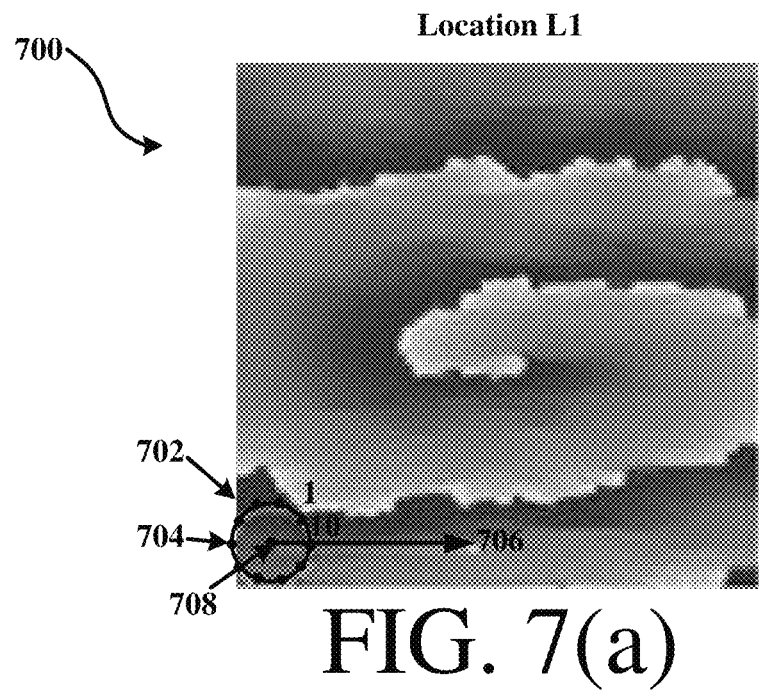
FIGS. 7(a)-7(f) (collectively referred to herein as "FIG. 7") provide a plurality of illustrations that are useful for understanding the method of FIG. 6.
Figure 7B:
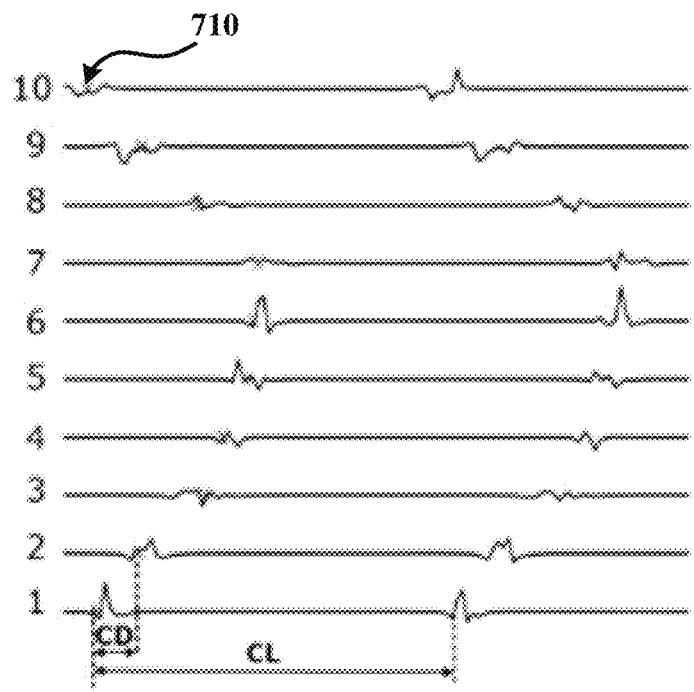
Figure 7C:
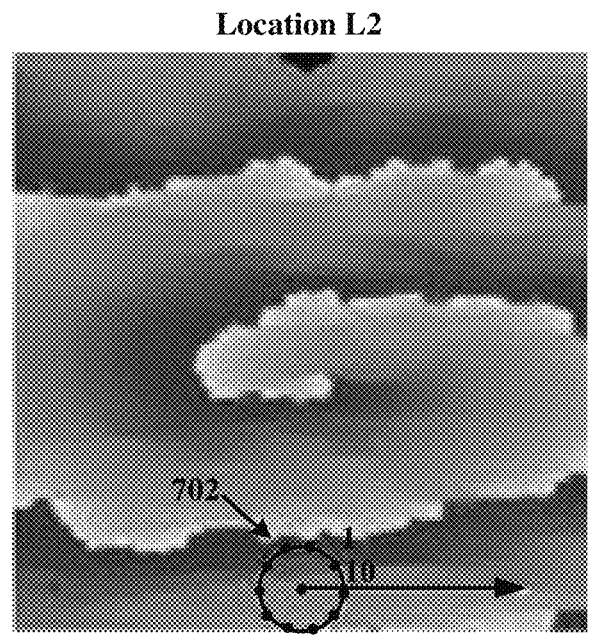

The MPDC electrogram signals are analyzed in 608 by the computing device to determine a PWD to a signal source and/or to identify which bipole electrode (e.g., bipole electrode 10 of FIG. 3) of the MPDC was activated first by the propagating wave. The identified bipole electrode is considered an FAB. For example, the raw electrogram signals of FIG. 7(b) are analyzed to identify the raw electrogram signal with the first fluctuation 710 from a reference value (positive or negative) during a given period of time. The bipole electrode associated with the identified raw electrogram signal is determined to be the FAB. The present solution is not limited to the particulars of this example.

In 610-614, a condition is considered for stopping the process. Operations are stopped when a stop condition is met. The stop condition is based on (a) at least one of a TCD divided by a CL, (b) a CW divided by CL, (c) TCD/CW, (d) characteristics of pattern of sensor movement, (e) the source's distance from a current sensor location, and/or (f) a source's distance from a previous sensor location. The stop condition is selected based on at least one of an amplitude of the plurality of signals and a target type.

In the first stop condition scenario (a), at least the following electrogram characteristics are obtained by the computing device: CL at the FAB; and a TCD. Techniques for obtaining electrogram characteristics are well known in the art. Any known or to be known technique can be used herein without limitation. Once the electrogram characteristics are obtained, the computing device performs the following computation in 612 to determine a value v.

$$v = TCD/CL$$

This value v is then used in 614 to determine if it is greater than a threshold value (e.g., 0.7). If the value v is greater than the threshold value (e.g., 0.7) [614:YES], then 616 is performed where method 600 ends or other processing is performed (e.g., return to 604). In contrast, if the value v is less than the threshold value (e.g., 0.7) [614:NO], then 618-622 are performed.

618-620 involve: determining a first recommended direction for movement of the MPDC based on the results of the analysis performed in 608 and/or an atrial anatomy; and determining a first recommended distance of travel for the MPDC based on the atrial anatomy. The first recommended direction is defined by a line extending from a center of the MPDC to the FAB identified in 608 (e.g., bipole electrode 10 as shown in FIG. 7(a)). The first recommended distance of travel is defined as half the distance of the remaining search area of the atria. The search area can be acquired using imaging techniques (such as CT and/or MRI), mapping techniques (such as electroanatomic mapping), and/or any other virtual area obtained using the specifications of a subjects's atrium. The search area can be a 2D area transformed from a 3D coordinate system, a 3D surface (where the coordinates of the vertices of the surface are known or the equation of the 3D surface is known), and/or any other geometrical representation. The search area can be expressed in any domain—continuous, discrete, etc.

Next in 622, an arrow is added to the display showing the first recommended direction and distance of travel for the MPDC. An illustration of an exemplary arrow 706 that has been added to the display is provided in FIG. 7(a). Notably, the arrow 706 starts at the center 708 of the circular indicator. The arrow 705 (a) extends in the PWD and/or (b) passes through the marking 704 representing the FAB (here bipole electrode 10). The arrow also extends away from the center 708 by an amount representative of the first recommended distance of travel.

Figure 6B:
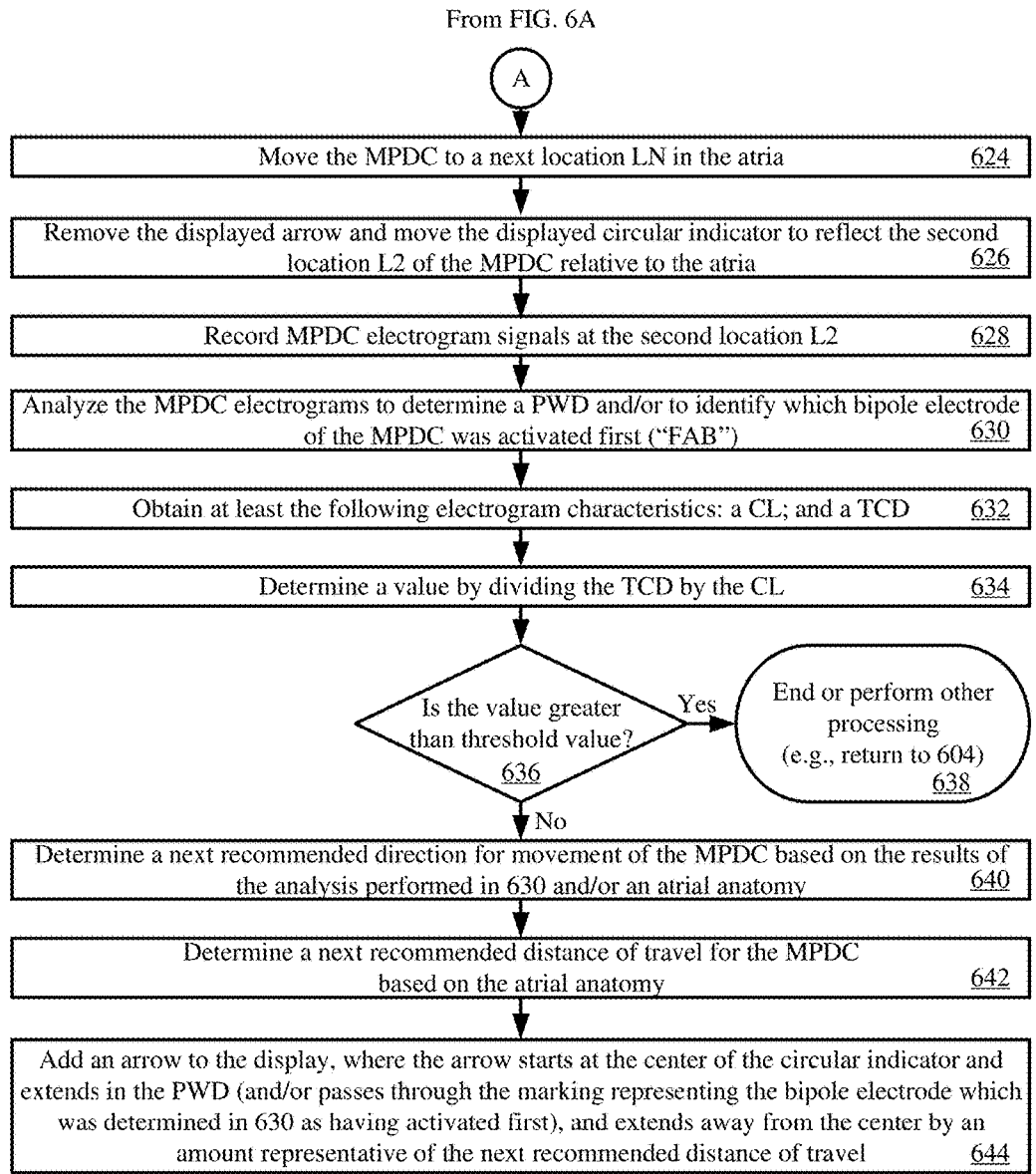

Upon completing 622, method 600 continues with 624 of FIG. 6B. As shown in FIG. 6B, 624 involves moving the MPDC to a next location LN (e.g., second location L2) in the atria, where N is an integer value greater than 1. In response to this movement of the MPDC, the displayed arrow is removed and the displayed circular indicator is moved to reflect the next location LN of the MPDC relative to the atria, as shown by 626.

MPDC unipolar electrogram signals are recorded in 628 while the MPDC is at the next location LN. The MPDC bipolar electrogram signals are computed and analyzed in 630 to determine a PWD and/or identify which bipole electrode of the MPDC was activated first (e.g., bipole electrode 8 of FIG. 3) by the propagating wave. The identified bipole electrode is considered the FAB. The operations performed in 630 are the same as or similar to those performed in 608.

In 632-636, a stop condition is considered. In some scenarios, at least the following electrogram characteristics are obtained by the computing device: CL; and a TCD. The operations performed in 632 are the same as or similar to those performed in 610. Once the electrogram characteristics are obtained, the computing device performs a computation to determine a value v, as shown by 634. This computation is discussed above in relation to 612.

Thereafter, a decision is made in 636 to determine if the value v is greater than a threshold value (e.g., 0.7). If the value v is greater than the threshold value [636:YES], then 638 is performed where method 600 ends or other processing is performed (e.g., return to 604). In contrast, if the value v is less than the threshold value [636:NO], then method 600 continues with 640-644.

640-642 involve: determining a second (or a next) recommended direction for movement of the MPDC based on the results of the analysis performed in 630 and/or atrial anatomy; and determining a second (or a next) recommended distance of travel for the MPDC based on a remaining search area of the atria. The second (or next) recommended direction is defined by a line extending from a center of the MPDC in the PWD or to the FAB identified in 630.

Next in 644, an arrow is added to the display showing the second (or next) recommended direction and distance of travel for the MPDC. An illustration of an exemplary arrow 720 that has been added to the display is provided in FIG. 7(d). Notably, the arrow 720 starts at the center 708 of the circular indicator, extends in the PWD, and extends away from the center 708 by an amount representative of the second (or next) recommended distance of travel.

Figure 7D:
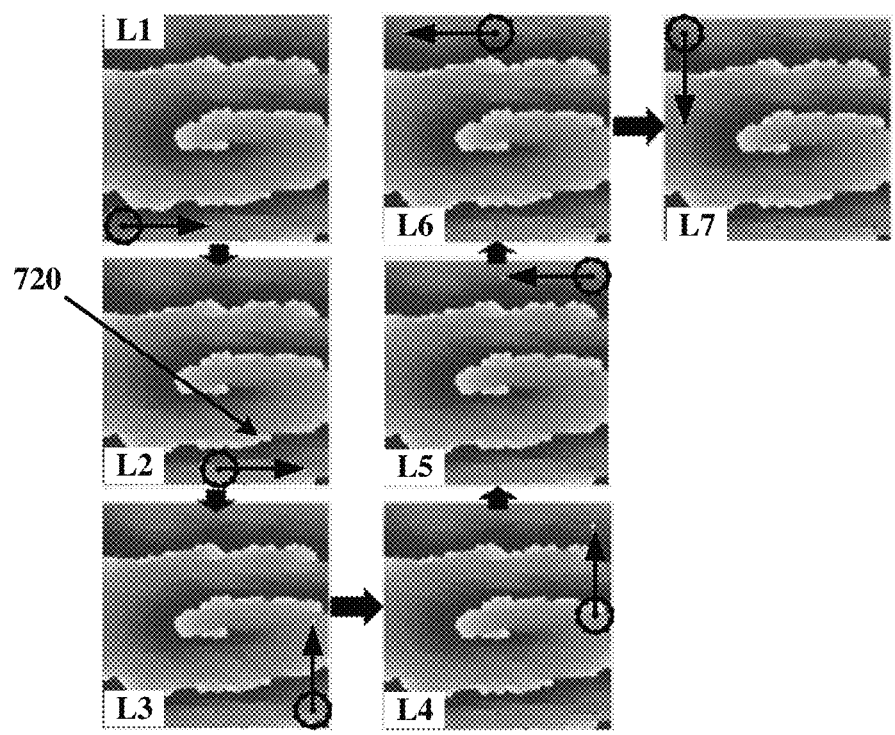
Figure 7E:
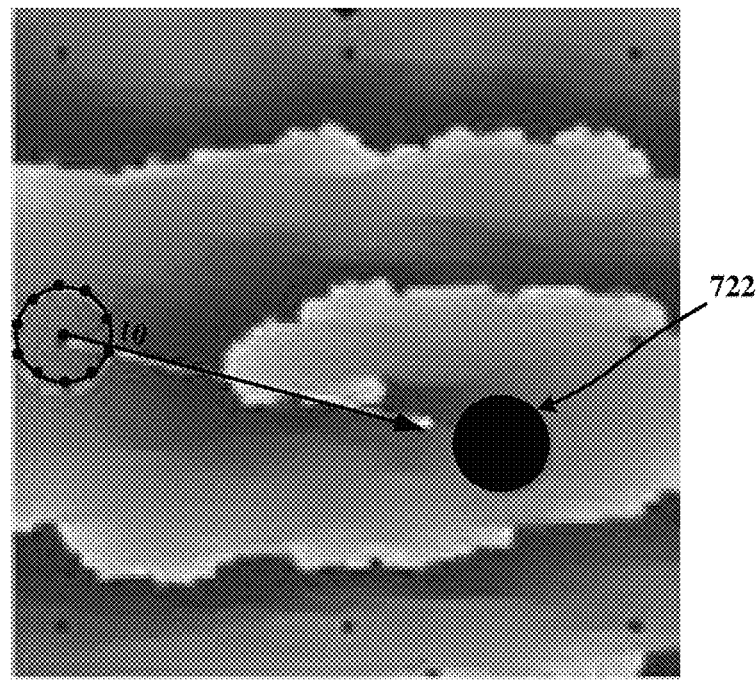

Upon completing 644, a decision is made in 646 of FIG. 6C. As shown in FIG. 6C, the decision is made to determine if a pre-defined number of iterations of the sensor movement has been performed. For example, as shown in FIG. 7(d), seven iterations of the sensor movement is performed such that the MPDC is moved to locations L1, L2, L3, L4, L5, L6 and L7. The present solution is not limited to the particulars of this example. Any number of iterations can be performed in accordance with a particular application.

Figure 7F:
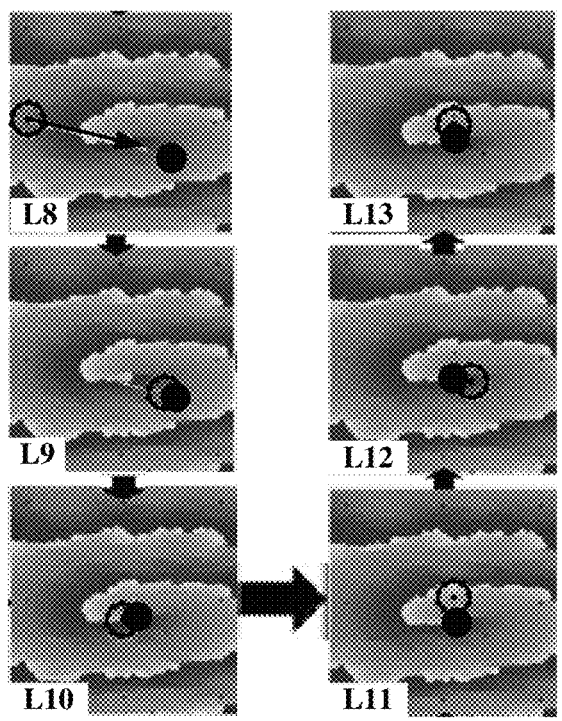

If the pre-defined number of iterations of sensor movement have not been performed (or if there are not enough points collected to make a decision) [646:NO], then 648 is performed where method 600 returns to 624 so that another iteration of 624-646 is performed. If the pre-defined number of iterations of sensor movement have been performed (or if there are enough points collected to make a decision) [646:YES], then method 600 continues with 650-654. 650-654 involve: using sensor data (e.g., MPDS electrogram information) to estimate a location of a propagating wave source; plotting the estimated location of the propagating wave source on a two dimensional graph having transparent grid lines; and overlaying the two dimensional graph on the image to that the estimated location of the propagating wave source in the atria is shown in the display. An illustration of a two dimensional graph overlaid on top of the image is provided in FIG. 7(e). Notably, the grid lines of the two dimensional graph are transparent. The grid has a dot 722 plotted thereon. The dot represents the estimated location of the propagating wave source in the atria. FIG. 7(f) shows a plurality of images having the two dimensional graph overlaid thereon. The present solution is not limited to the particulars of FIGS. 7(e)-7(f).

Referring again to FIG. 6C, method 600 continues with 656 where the MPDC is moved to the location provided by the output of the filer in 816. In response to this movement of the MPDC, the displayed arrow is removed and the displayed circular indicator is moved to reflect the next location LN of the MPDC relative to the atria, as shown by 658. FIG. 7(f) shows the MPDC moved to a plurality of sequentially estimated locations of the propagating wave source.

MPDC unipolar electrogram signals are recorded in 660 while the MPDC is at the next location LN. The MPDC bipolar electrogram signals are computed and analyzed in 662 to determine a PWD and/or to identify which bipole electrode of the MPDC was activated first (e.g., bipole electrode 8 of FIG. 3) by the propagating wave. The identified bipole electrode is considered the FAB. The operations performed in 662 are the same as or similar to those performed in 608.

In 664-668, a stop condition is considered. In some scenarios, at least the following electrogram characteristics are obtained by the computing device: CL; and a TCD. The operations performed in 664 are the same as or similar to those performed in 610. Once the electrogram characteristics are obtained, the computing device performs a computation to determine a value v, as shown by 666. This computation is discussed above in relation to 612.

A decision is made in 668 as to whether or not the value v is greater than the threshold value. If the value is greater than the threshold value [668:YES], then method 600 ends or other processing is performed as shown by 670. In contrast, if the value is not greater than the threshold value [668:NO], then method 600 returns to 650 as shown by 672 so that another iteration of the source location estimation process is performed. FIG. 7(f) shows a plurality of images with a final location MPDC location L13.

In view of the forgoing, the present solution generally concerns implementing systems and methods for guiding the movement of a sensor in an object or space. For example, in some scenarios, an MPDC is guided in an atria to develop an AF ablation target map. The ablation target map reveals the locations of any AF sources in the atria. The AF sources may include the propagating wave of bioelectricity that circulates in the tissue as a scroll wave or spiral (referred to as a rotor and shown in FIG. 7) or repetitive focal wave propagation (referred to as a foci). Characteristic(s) of recorded electrogram signals are used to decide on the location of the next movement of the MPDC. The present solution can be used in the left or right atrium depending on the clinical needs. The present solution is not limited to the particulars of this AF based example.

The use of the present solution in MPDC applications has many advantages. For example in the MPDC application, the present solution is based on MPDC catheters (e.g., Lasso and/or Pentaray) that are routinely used in AF ablation procedures, and therefore does not require any specific equipment or type of catheter (such as basket catheters). As a result, the present solution will not enforce any additional risks or costs to the patients. Furthermore, MPDCs provide high resolution mapping of the atria and good quality of the electrogram recordings. Basket catheters have limited torque capabilities and limited maneuverability which hamper correct placement. Basket catheters can also abrade the endocardium.

The present solution provides a means to guide the placement of an MPDC in the atria to locate the AF sources (rotors and foci). Some conventional methods do involve an MPDC to detect the presence of an AF source in the atria, but they are based on random placements of the MPDC, i.e., there is no guidance of MPDC placement as is done in the present solution. As noted above, this guidance of MPDC placement is provided by the present solution via an AF ablation target map. The AF ablation target map provides a visual feedback for the clinicians in the electrophysiology laboratory as they perform an AF ablation procedure. The AF ablation target map can be used to delineate one AF source at a time or to delineate the regions of multiple AF sources at any given time. The type of AF source(s) (e.g., rotor, foci or other type) and/or the probability of an AF source at each delineated region may be provided along with the AF ablation target map. The AF ablation target map may be a 2D or 3D map which is quickly and effectively generated via the present solution.

The present solution may also be used in guiding of the ablation therapy in ventricular arrhythmias. In this case, a catheter is guided to locate reentrant or focal sources in ventricular tachycardia. In those or other scenarios, the present solution may use anatomic constraints of the heart to help guide the MPDC placement. For example, details about an atrium anatomy can be input into the computing device. These details can include, but are not limited to, the structure of the anatomy (e.g., left or right atrium), the structure or orientation of pulmonary veins, and/or the structure or orientation of an autonomic ganglia.

As noted above, the present solution provides a means for guiding a sensor placement. The guidance algorithm needs the following two inputs: direction; and distance. The direction and the distance can be produced by multiple techniques. For example, in FIG. 6, the FAB is used to give the direction and the search area is used to give the distance. The distance can additionally or alternatively comprise: a radius distance; a distance produced by a probabilistic (e.g., Likelihood methods) or Bayesian algorithm; a distance produced using a known/assumed model; a distance produced using a learned model (using parameter/machine learning approaches); an arbitrary distance value (such as half the maximum distance); and/or an estimated distance value.

In some scenarios, the guidance information of the system is represented on a target map as described above. Additionally or alternatively, the guidance information is represented on an anatomic map. For example, the guidance information is represented as: a sequential and final map (i.e., a visual target vs non-target map of the source region that gets updated with every move, and final delineated region of the source location); a pin pointed location map (another form of indication is to pinpoint the source location in the map, as opposed to a delineated region); a probabilistic map (i.e., a map illustrating the probability of an AF source being present at each location); and/or other visual representation of the source region or location.

Referring now to FIG. 8, there is provided an illustration that is useful for understanding a process 800 for guiding a sensor (e.g., MPDC 110 of FIG. 1) to a target location (e.g., location L13 of FIG. 7(f)) in accordance with the present solution. As shown in FIG. 8A, the process involves performing the following operations: PWD operations 802; Point Cloud ("PC") formation operations 804; Clustering and Noise ("C/N") removal operations 806; Check Prior Threshold ("CPT") operations 808; Guide-To-Anatomy ("GTA") based observation operations 810; and operations 812 to guide sensor based on estimated target location. Operations 802-812 are performed to determine where to plot a dot (e.g., dot 722 of FIG. 7(e)) on a grid. The dot represents the estimated location of the propagating wave source in the atria.

During use, operations of blocks 802-810 are performed for a certain number of iterations (e.g., iterations L1-L7 of FIG. 7(d)) until a particular criteria is met. Once that particular criteria is met, the process 800 continues with from block 808 to block 812. The particular criteria includes, but is not limited to, a number of iterations performed and/or a number of points in a cluster.

Electrogram signals are input into block 802. The electrogram signals are processed in block 802 to determine a PWD or an estimated direction to the propagating wave sources relative to the sensors current location. The PWD is then provided to block 804 where an attempt is made to generate a point cloud. If only one PWD has been provided to 804 (e.g., when a single iteration of operations 802-810 has been performed), then there are not enough points to generate a point cloud. In this case, the prior threshold of block 808 is not met (e.g., seven points have not yet been determined based on electrogram signals obtained at sensor locations L1-L7 of FIG. 7(d)). So, the process continues to 810 where the sensor is guided to a next location based on the anatomy.

In contrast, when a certain number of points have be determined to create a point cloud, the point cloud is provided to bock 806. In block 806, the points in the point cloud are grouped into one or more clusters. Point cloud and cluster information is then provided to block 812 where it is used to guide the sensor based on an estimated target location.

Figure 8B:
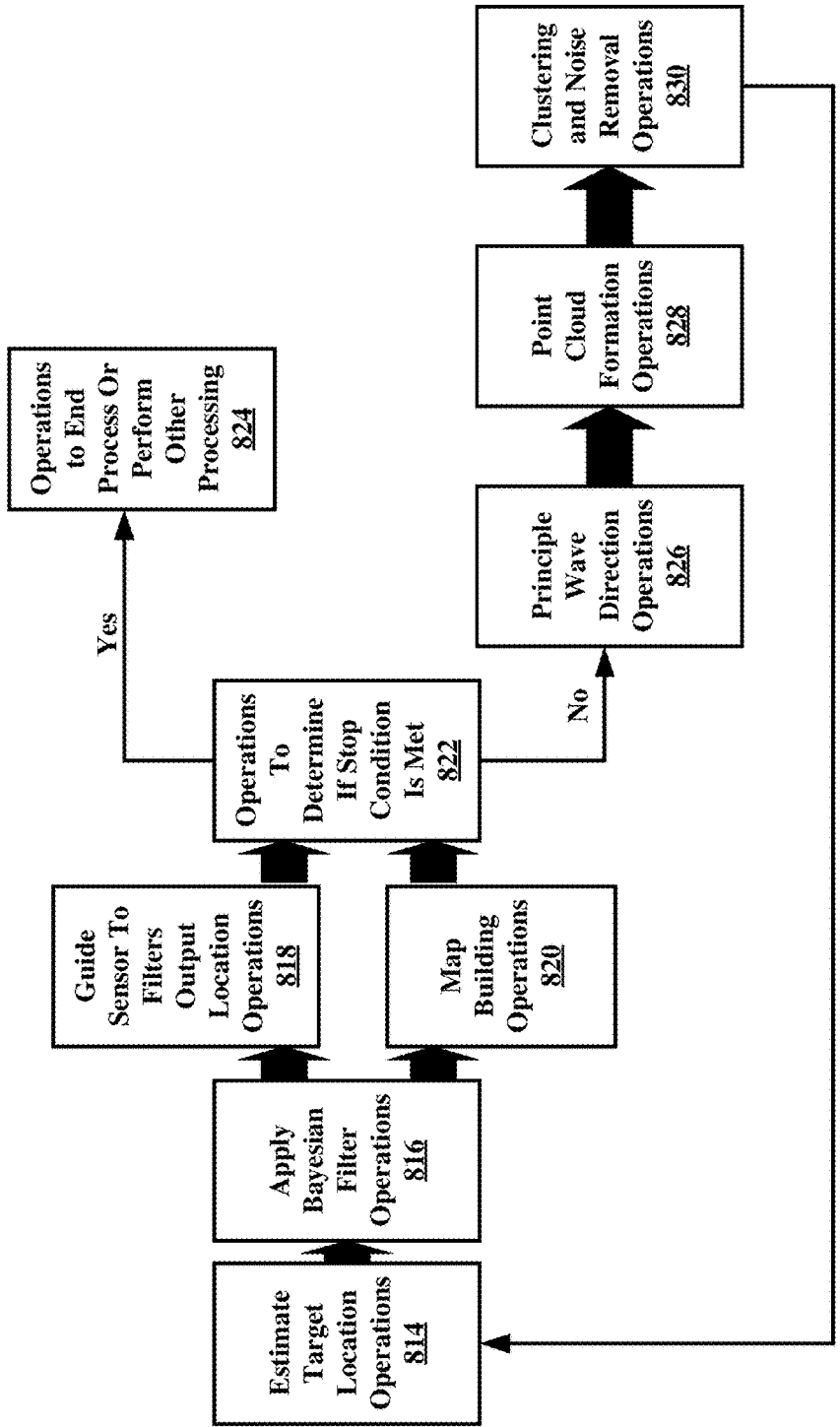

As shown in FIG. 8B, the operations of block 812 include: operations 814 to determine an estimate target location value; Bayesian filter operations 816 to determine a more accurate estimate target location value; operations 818 to guide the filter to the more accurate estimate target location value; and operations 820 to build a map (i.e., plot a dot 722 on a grid).

Upon completing 818 and 820, operations of block 822 are performed to determine if a stop condition is met. The stop condition can be based on TCD/CL, Cycle Width ("CW") divided by CL, TCD/CW, characteristics of pattern of sensor movement, distance(s) from current sensor location and previous sensor location(s), and/or any other threshold values. The stop condition is selected in accordance with a particular application. For example, the stop condition is selected based on an amplitude of electrogram signals and/or a target type.

If the stop condition is met (e.g., TCD/CL is greater than a threshold value) [822:YES], operations of block 824 are performed by which process 800 ends or other processing is performed. In contrast, if the stop condition is not met [822:NO], operations of blocks 826-830 are performed. The operations of blocks 826-830 are the same as or substantially similar to the operations of blocks 802-806 of FIG. 8A. Upon completing the operations of 830, process 800 returns to 814 so that another iteration thereof is performed.

A more detailed illustration of the PWD operations 802 is provided in FIG. 9. The PWD operations 802 generally involve analyzing pairs of electrogram signals to determine a plurality of PWDs and computing an average of the PWDs.

As shown in FIG. 9, the PWD operations 802 comprise operations 902 to determine electrogram signal activation times. Operations 902 generally involve analyzing electrogram signals to determine times at which respective sensors were activated. For example, the electrogram signals of FIG. 7(b) are analyzed to detect when amplitude changes 710 occur in each electrogram signal. Once the electrogram signal activation times are detected, optional operations 904 are performed to pre-process data specifying the activation times. The pre-processing can include, but is not limited to, filling in missing data and/or removing data having values falling outside pre-defined ranges.

Next in block 906, operations are performed to find temporally adjacent pair vectors based on the activation times. Temporally adjacent pair vectors are those vectors associated with two electrogram signals that activated sequentially in time. For example, with reference to FIG. 7(b), temporally adjacent pair vectors are those vectors associated with: (a) electrogram signals 1 and 10; (b) electrogram signals 2 and 9; (c) electrogram signals 3 and 8; (d) electrogram signals 4 and 5; and (e) electrogram signals 6 and 7. Illustrations are provided in FIG. 10 which are useful in understanding what constitutes temporally adjacent sensor pairs. Each image of FIG. 10 includes a plurality of block solid lines 1012. Each line 1012 extends between two sensors associated with temporally adjacent pair vectors.

Figure 10:
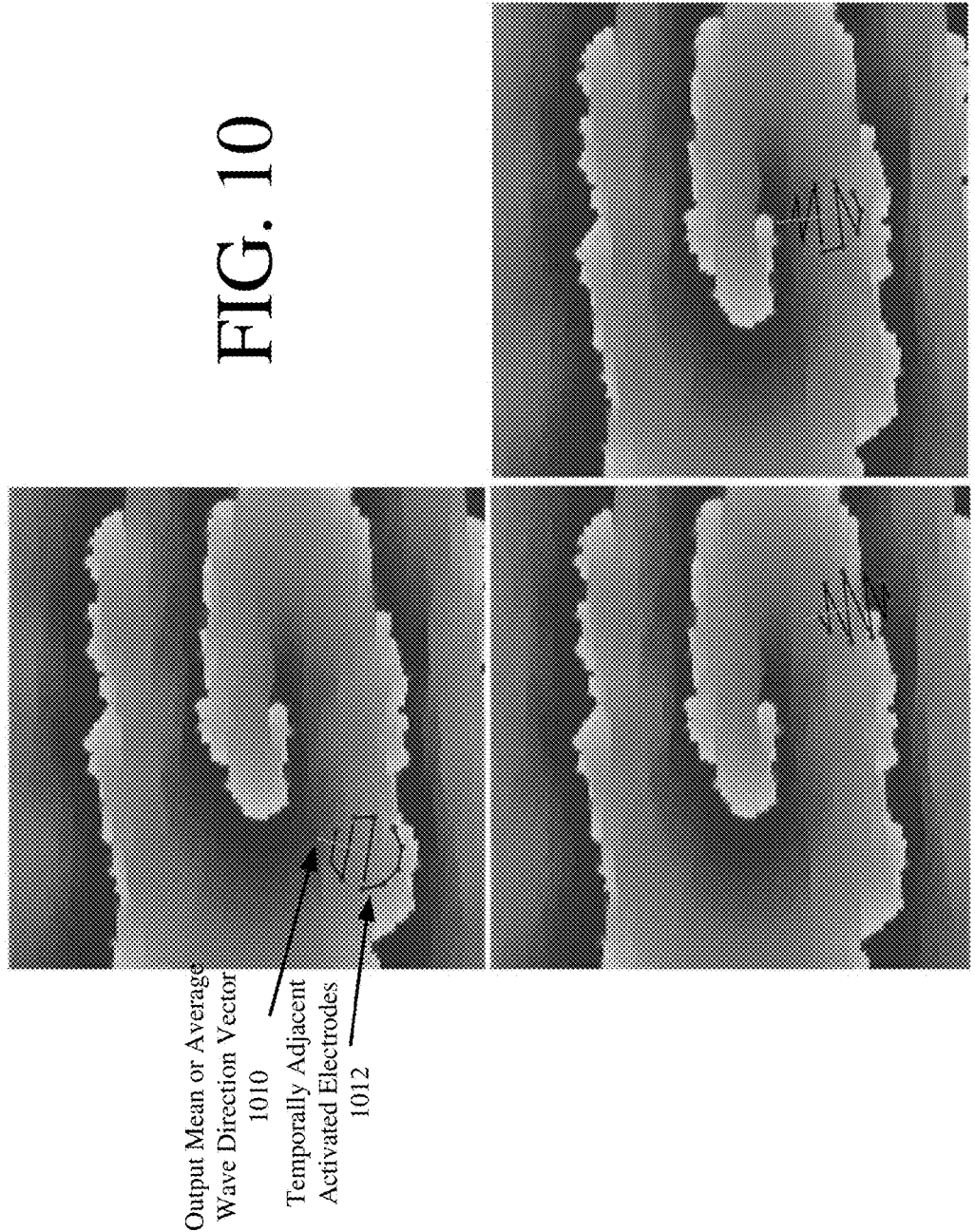
FIG. 10 provides images that are useful for understanding the PWD operations of FIGS. 8-9.

Referring again to FIG. 9, the process continues with operations of block 908 to final normal vectors of temporally adjacent pair vectors. In block 910, operations are performed to find the mean or average wave direction of normal vectors. Subsequently, the mean or average wave direction is output as shown by block 912. An illustrative mean or average wave direction 1010 is shown in FIG. 10.

In some scenarios, the operations 902-212 are defined by the following mathematical equations.
t→Activation times
$t_i = \{t_1, t_2, \ldots, t_{10}\}$→Sorted from earliest to latest
bipole $t_i = (x_1, t_2) \to i^{th}$ bipole coordinates in Cartesian
Ia. Find bipole vectors $$\vec{d}_i = [x_{i+1} - x_i, y_{i+1} - y_i]_{i=1 \text{ to } 9}$$

Ib. Find normal of non-consecutive bipoles $$\vec{N} = \text{Normal}(\vec{d_1})|_{bipoles \, non-consecutive}$$

Ic. Find mean of normal $$\vec{V}_{PWD} = \text{mean}(\vec{N})$$

The present solution is not limited to the particulars of the above mathematical equations.

Figure 11:
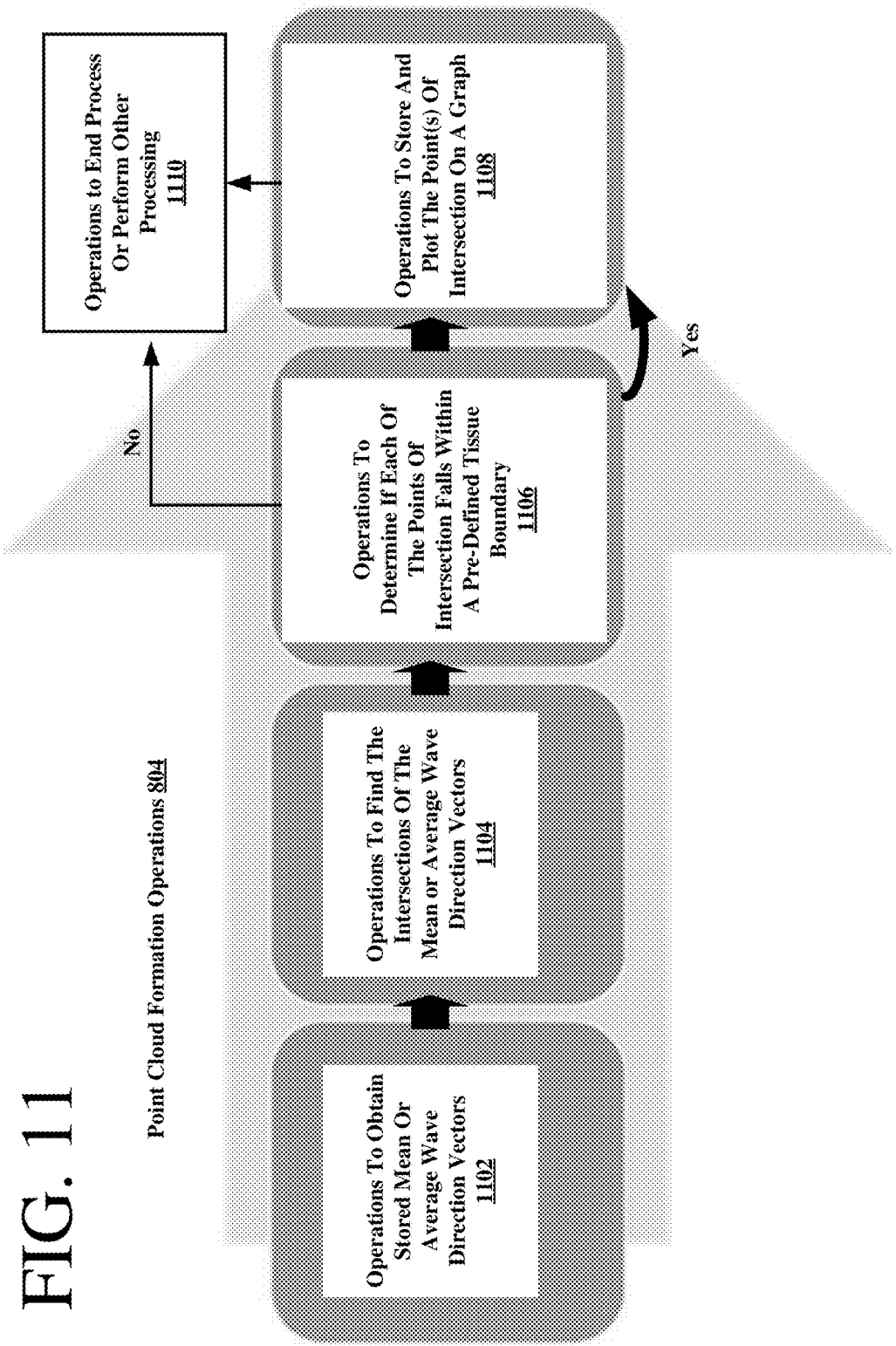
FIG. 11 provides an illustration that is useful for understanding point cloud formation operations of FIG. 8.
Figure 12:
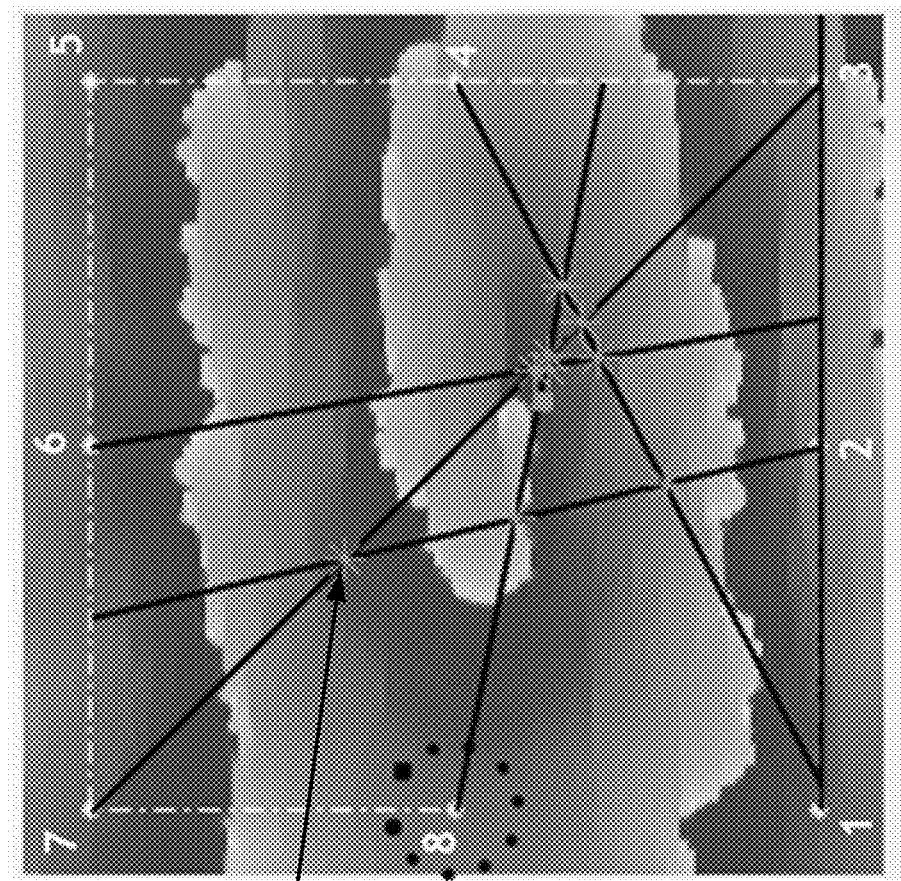
FIG. 12 provides an illustration that is useful for understanding point cloud formation operations of FIGS. 8 and 11.

Referring now to FIG. 11, the PC formation operations 804 generally involve operations 1102 to obtain the mean or average wave direction vector(s) output from PWD operations 802. Operations 1102 may involve accessing a memory to read stored mean or average wave direction vector(s) therefrom. Next in block 1104, operations are performed to find the intersections of the mean or average wave direction vectors. A determination is then made in 1106 to determine if each of the points of intersection falls within a pre-defined tissue boundary. If so [1106:YES], then operations are performed to store and plot the point(s) of intersection on a graph, as shown by 1108. An illustration showing points of intersection 1200 plotted on a graph is provided in FIG. 12. Next in 1110, the process ends or other processing is performed. If not [1106:NO], then 1110 is performed.

In some scenarios, the PC formation operations are defined by the following mathematical equations.

$$\vec{V}_{PWD-R} = [\vec{V}_{PWD-1}, \vec{V}_{PWD-2}, \ldots, \vec{V}_{PWD-N}]$$

where R is the intersection number.

$$P_R = \text{intersection}(V_{PWD-R})|_{P_R < \text{tissue boundary}}$$

where $P_R$ is the point clouds. The present solution is not limited to the particulars of the above mathematical equations.

Figure 13:
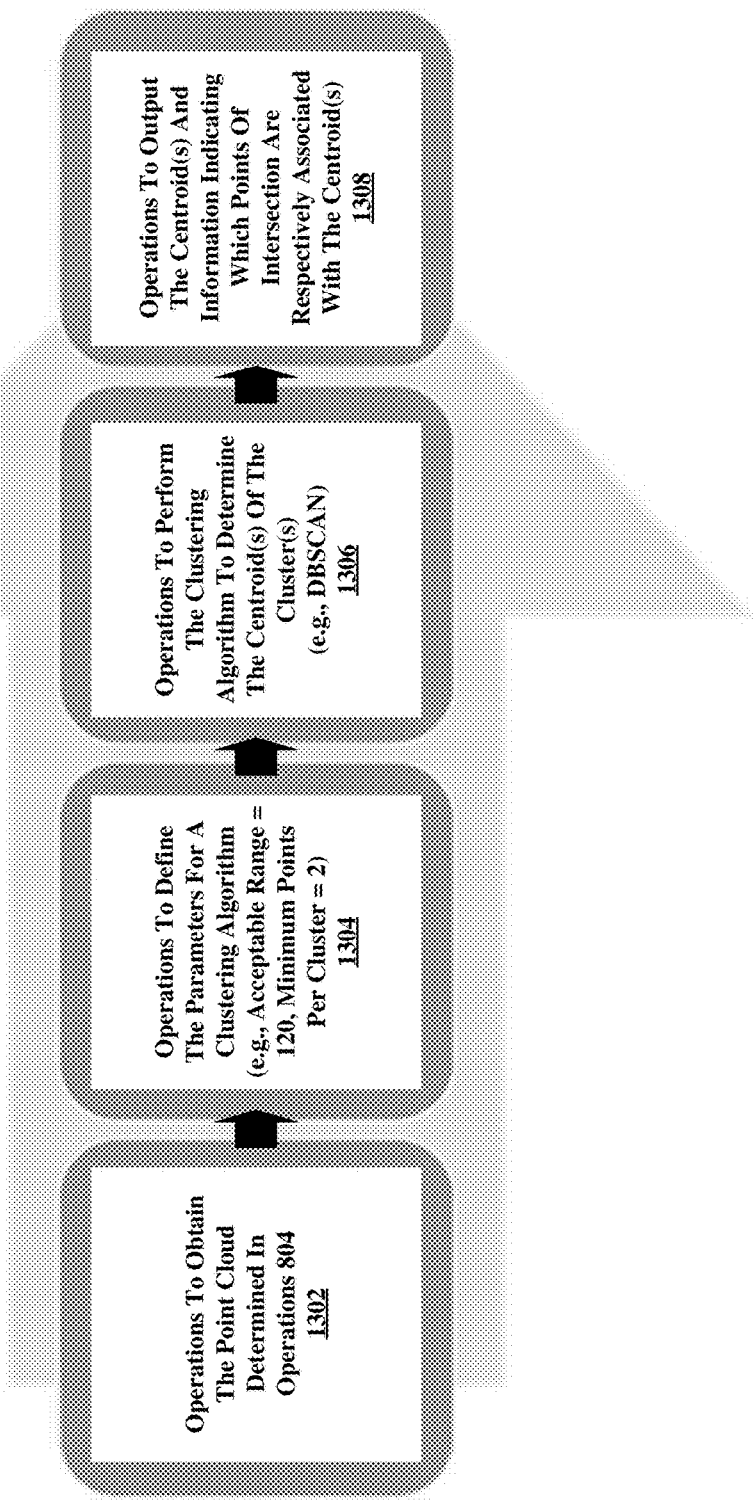
FIG. 13 provides an illustration that is useful for understanding clustering and noise removal operations of FIG. 8.
Figure 14:
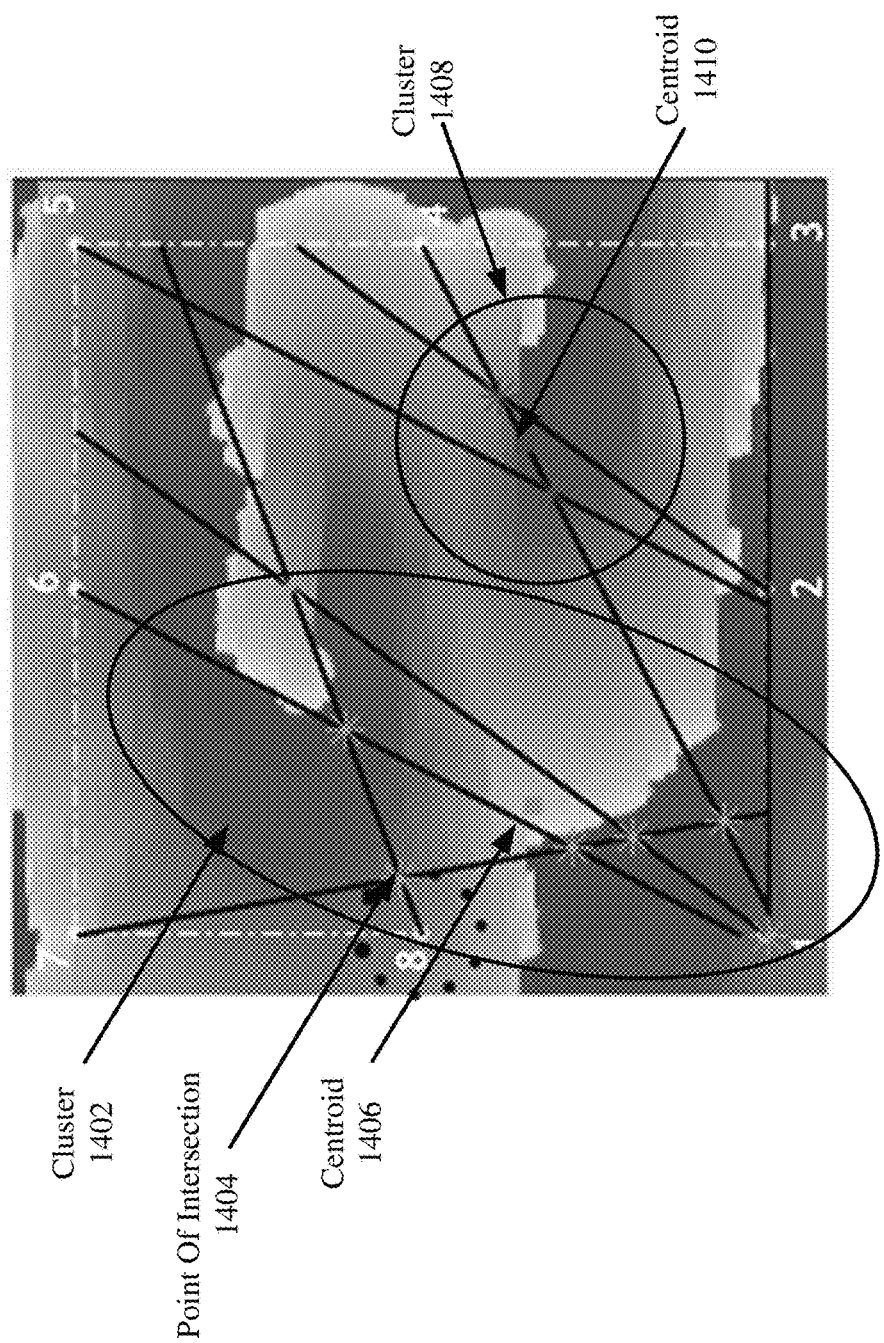
FIG. 14 provides an illustration that is useful for understanding clustering and noise removal operations of FIGS. 8 and 13.

Referring now to FIG. 13, the C/N removal operations 806 include operations 1302 to obtain the point cloud determined in the PC formation operations 804. Next in 1304, operations are performed to define the parameters for a clustering algorithm. Such parameters can include, but are not limited to, an acceptable range and a minimum number of points per cluster. Clustering algorithms are well known in the art. Any known or to be known clustering algorithm can be used herein without limitation. In some scenarios, a Density Based Spatial Clustering of Applications with Noise ("DBSCAN") algorithm is employed. The clustering algorithm is performed in 1306 to determine the centroid(s) of the cluster(s). Information specifying the centroid(s) and indicating which points of intersection are respectively associated with the centroid(s) is output in 1308. An illustration showing two clusters 1402, 1408 with points of intersection 1404 and centroids 1406, 1410 is provided in FIG. 14.

In some scenarios, the C/N removal operations can be defined by the following mathematical equations.

$$E = 120, N_{points} = 2$$

$$C_P = \text{DBSCAN}(P_R, E, N_{PMIN})$$

where $C_P$ is the cluster of points $P_R$. The present solution is not limited to the particulars of the above mathematical equations.

Figure 15:
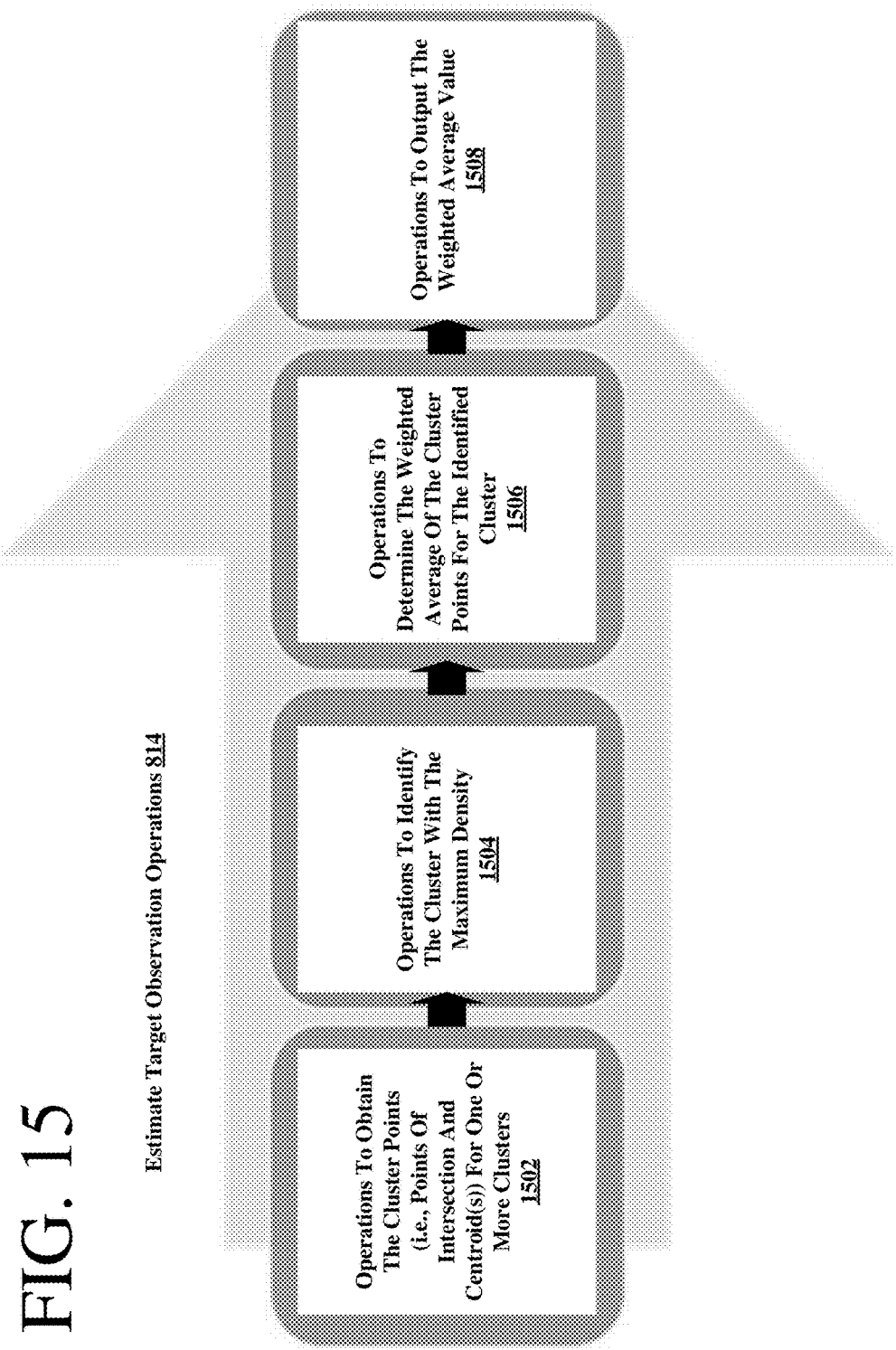
FIG. 15 provides an illustration that is useful for understanding estimate target observation operations of FIG. 8.
Figure 16:
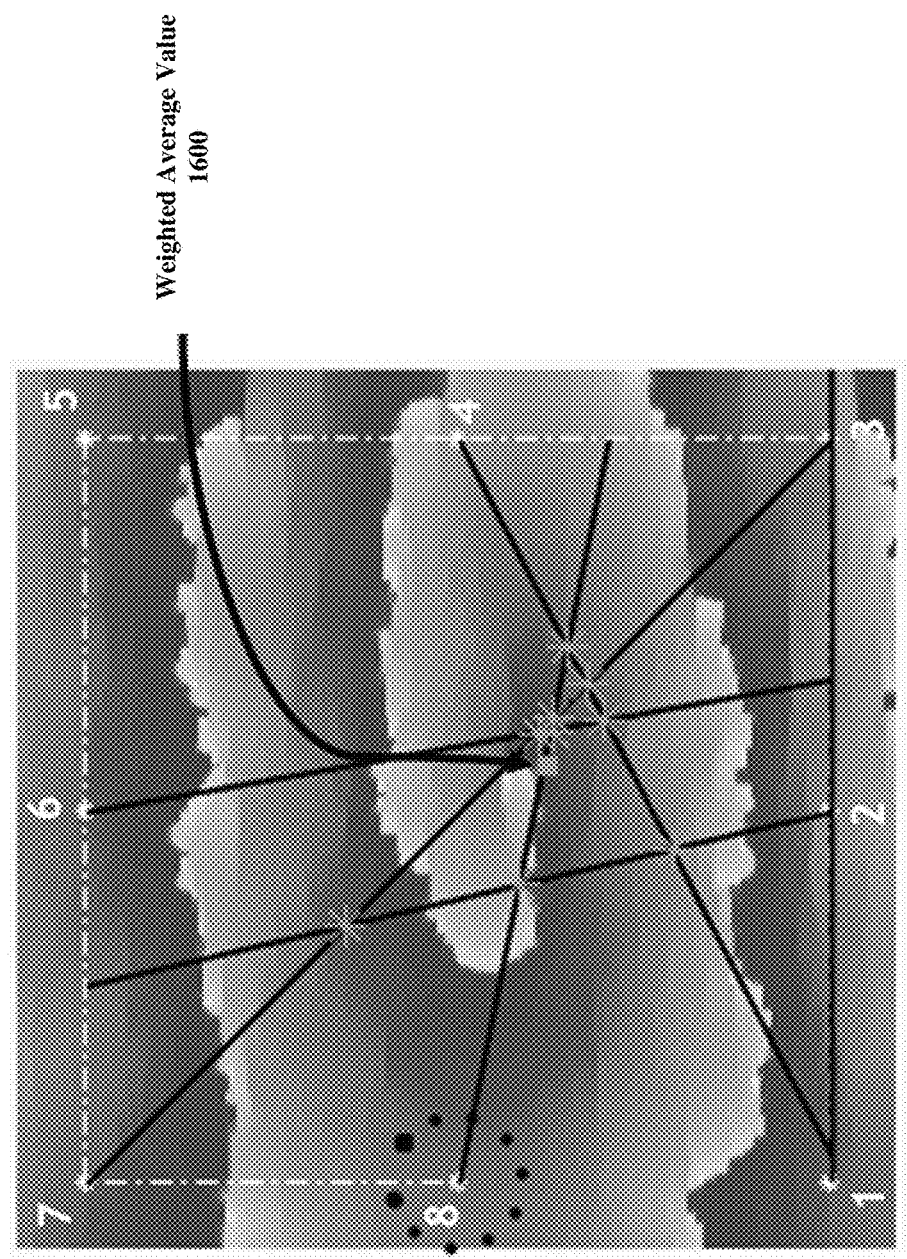
FIG. 16 provides an illustration that is useful for understanding estimate target observation operations of FIGS. 8 and 15.

Referring now to FIG. 15, the CPT operations 808 generally involve obtaining the cluster points for one or more clusters, as shown by 1502. The cluster points include the points of intersection and the centroid(s). Next in 1504, operations are performed to identify the cluster with the maximum density. This cluster can include the cluster with the greatest total number of points. The weighted average of the cluster points for the identified cluster is then determined in 1506. Methods for determining weighed averages of cluster points are well known in the art. Any known or to be known weighted averaging technique can be used herein without limitation. The values of the weighted average is then output as shown by 1508. An illustration showing an illustrative weighted average value 1600 is provided in FIG. 16.

The ETO operations 814 generally involve estimating a target location or a propagating wave source location. In some scenarios, the ETO operations are defined by the following mathematical equations.

$$X_R = \text{WeightedMean}(P_R | \max_{N_P}(C_{P_x}))$$

where $X_R$ represents the cartesian coordinates (x, y) and $P_R | \max_{N_f}(C_{P_x})$ represents points in a cluster with maximum density. The present solution is not limited to the particulars of the above mathematical equations.

Figure 17:
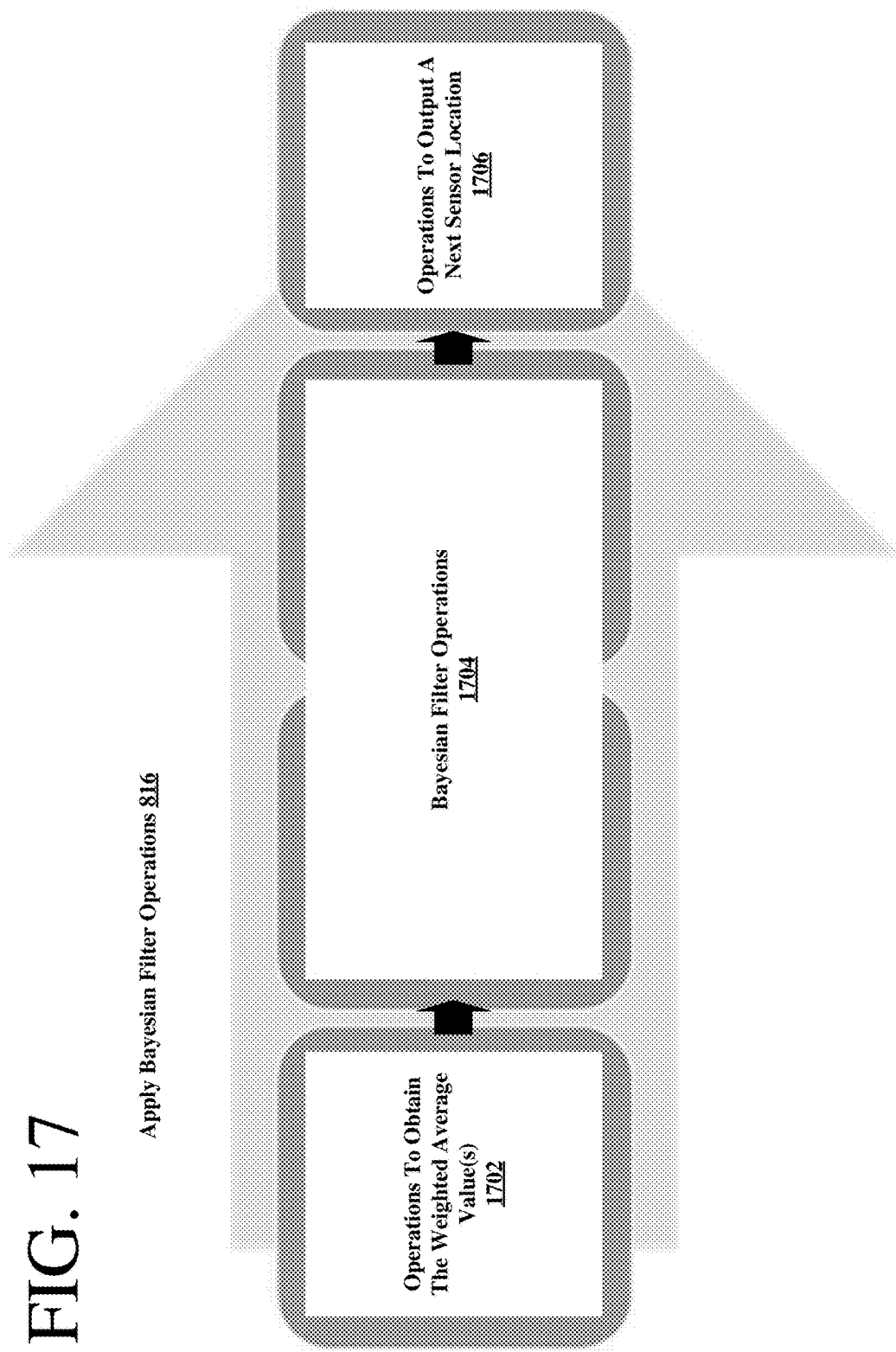
FIG. 17 provides an illustration that is useful for understanding Bayesian filter operations of FIG. 8.
Figure 18:
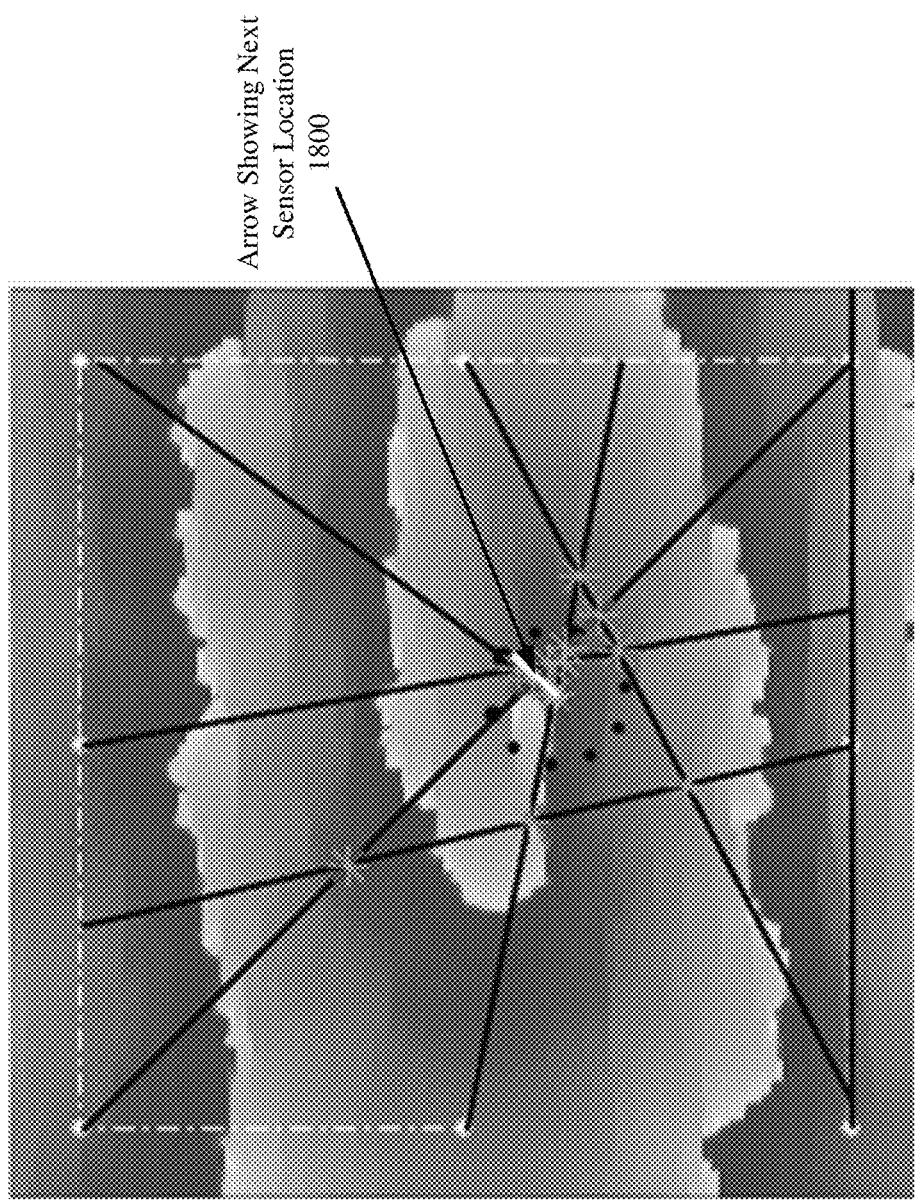
FIG. 18 provides an illustration that is useful for understanding Bayesian filter operations of FIGS. 8 and 17.

Referring now to FIG. 17, there ABF operations 816 generally involve performing operations 1702-1706 to obtain the weighted average value(s), a next sensor location via Bayesian filtering of the weighted average value(s), and output the next sensor location. An illustration showing an illustrative next sensor location 1800 is provided in FIG. 18.

In some scenarios, the ABF operations are defined by the following mathematical equations for a modified Kalman filter.

$$P_{S-1} = \begin{bmatrix} 900 & 0 \\ 0 & 900 \end{bmatrix}, X_{S-1} = X_S, Q_S = \begin{bmatrix} 0 & 0 \\ 0 & 0 \end{bmatrix}$$

$$u_S = 0, f_S = \begin{bmatrix} 1 & 0 \\ 0 & 1 \end{bmatrix}, B_S = \begin{bmatrix} 1/2 \\ 1/2 \end{bmatrix}$$

Prior (S=1$^{st}$ iteration after prior threshold is reached)

$$X_S = f_S X_{S-1} + B_S u_S$$

Posterior (R=All iterations after prior step above).

$$S_S = \begin{bmatrix} 100 & 0 \\ 0 & 100 \end{bmatrix}, H_S \begin{bmatrix} 1 & 0 \\ 0 & 1 \end{bmatrix}, Z_S = X_S$$

$$K = P_S H_S [(H_S P_S H_S') + R_S]_{-1}$$

$$X_{S+1} = X_S + (K(Z_S - H_S X_S)$$

$$P_{S+1} = P_S - YK(H_S P_S)$$

where Y is a modification to a Kalman filter (Y=0.5). The present solution is not limited to the particulars of the above mathematical equations. Notably, this is not a Kalman filter since the linear characteristics are lost due to the introduction of the variable Y.

Figure 19:
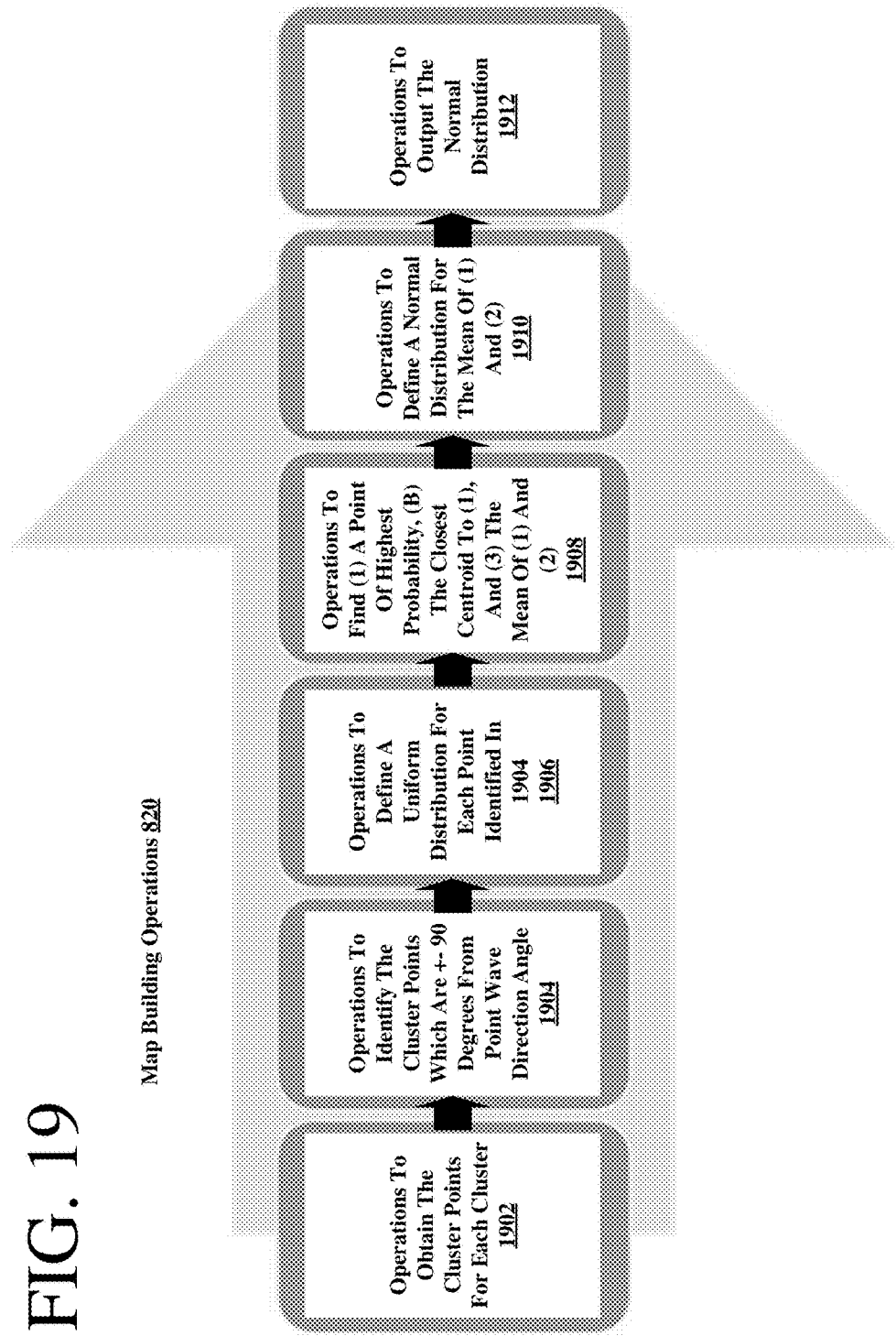
FIG. 19 provides an illustration that is useful for understanding map building operations of FIG. 18.

Referring now to FIG. 19, the map building operations 820 generally involve plotting a dot on a graph representing the estimated location of the target or propagating wave source. In this regard, operations are performed in 1902 to obtain the cluster points for each cluster. The cluster points include the points of intersection. The cluster points are used in 1904 to identify the points which are +−90 degrees from the PWD angle. A uniform distribution for each point identified in 1904 is then determined in 1906. Next in 1908, operations are performed to find (1) a point of highest probability, (2) the closest centroid to the point of highest probability, and (3) the mean of the point of highest probability and the closest centroid to the point of highest probability. A normal distribution for the mean (3) is defined in 1910. Subsequently in 1912, the normal distribution is output. An illustration shown an illustrative point of normal distribution 2000 is provided in FIG. 20.

In some scenarios, the map building operations are defined by the following mathematical equations.

$$f(P_R^1) = \text{Uniform}(P_{R,30}^1)$$

$$[x_M, y_M] = \arg\max(f(P_R^1))$$

$$[x_C, y_C] = \arg\min(\text{distance}([x_M, y_M], u_C))$$

$$u_M = \text{mean}([x_M, y_M], [x_C, y_C])$$

$$X_{target} = N(u_M, \sigma_M) | X_{target} > e^{-4}$$

where $X_{target}$ represents the x-y Cartesian coordinates for the estimated target location, $C_P$ represents the cluster of points, $P_R$ represents a point cloud, $P_R^1 = P_R$ in $\overrightarrow{v}_{pwn} \pm 90°$, $u_C$ is the centriod of each cluster ($u_C$=Centroid($C_P$))∀C. and $$\sigma_M = \begin{bmatrix} 4.5 \text{ cm} & 0 \\ 0 & 4.5 \text{ cm} \end{bmatrix}.$$

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application. Thus, the breadth and scope of the present invention should not be limited by any of the above described embodiments. Rather, the scope of the invention should be defined in accordance with the following claims and their equivalents.

What is claimed is:

1. A method for guiding a sensor to a location of a propagating wave source, comprising:
   receiving, by a computing device, a plurality of signals generated by a plurality of electrodes of the sensor while the sensor resides at the first location in the object;
   processing, by the computing device, the plurality of signals to determine coordinates of an estimated location of the propagating wave source relative to the first location at which the sensor resides; and
   providing a visual aid facilitating sensor movement by plotting a mark on a grid overlaid on top of an object image displayed by the computing device, wherein the mark (1) indicates an estimated location of the propagating wave source in the object and (2) is defined by a probability distribution based on a mean of (a) a given point in a point cloud generated based on principle wave direction values and (b) a centroid of a plurality of cluster centroids that is closest to the given point in the point cloud.

2. The method according to claim 1, further comprising guiding the sensor movement to a second location in the object based on an anatomy until a pre-defined criteria is met.

3. The method according to claim 2, wherein the pre-defined criteria comprises at least one of a number of iterations performed and a number of points in a cluster.

4. The method according to claim 1, further comprising stopping operations when a stop condition is met, where the stop condition is based on at least one of a Total Conduction Delay ("TCD") divided by a Cycle Length ("CL"), a Cycle Width ("CW") divided by CL, TCD/CW, patterns of previous mark locations on the grid, the source's distance from a current sensor location, and a source's distance from a previous sensor location.

5. The method according to claim 4, wherein the stop condition is selected based on at least one of an amplitude of the plurality of signals and a target type.

6. A method for guiding a sensor to a location of a propagating wave source, comprising:
   receiving, by a computing device, a plurality of signals generated by a plurality of electrodes of the sensor while the sensor resides at the first location in the object;
   processing, by the computing device, the plurality of signals to determine coordinates of an estimated location of the propagating wave source relative to the first location at which the sensor resides; and
   providing a visual aid facilitating sensor movement by plotting a mark on a grid overlaid on top of an object image displayed by the computing device;
   wherein the processing comprises:
      using the plurality of signals to determine a Principle Wave Direction ("PWD") to the propagating wave source; and
      using the PWD to determine if there are enough points to generate a point cloud.

7. The method according to claim 6, further comprising guiding the sensor to a next location in the object based on an anatomy if it is determined that there are not enough points to generate the point cloud.

8. The method according to claim 6, further comprising generating the point cloud if it is determined that there are enough points to generate the point cloud.

9. The method according to claim 8, further comprising grouping the points of the point cloud into at least one cluster.

10. The method according to claim 9, further comprising using the point cloud and the at least one cluster to determine coordinates of the mark.

11. The method according to claim 9, wherein the coordinates are determined by:
    identifying a cluster with a maximum density;
    determining a weighted average of the identified cluster's points; and
    performing a Bayesian filter algorithm using the weighted average to determine a next location in the object to where the sensor should be moved.

12. A system, comprising:
    a processor; and
    a non-transitory computer-readable storage medium comprising programming instructions that are configured to cause the processor to implement a method for guiding a sensor to a location of a propagating wave source, wherein the programming instructions comprise instructions to:
       receive a plurality of signals generated by a plurality of electrodes of the sensor while the sensor resides at the first location in the object;
       process the plurality of signals to determine coordinates of an estimated location of the propagating wave source relative to the first location at which the sensor resides; and
       provide a visual aid facilitating sensor movement by plotting a mark on a grid overlaid on top of an object image displayed by the system, where the mark (1) indicates an estimated location of the propagating wave source in the object and (2) is defined by a probability distribution based on a mean of (a) a given point in a point cloud generated based on principle wave direction values and (b) a centroid of a plurality of cluster centroids that is closest to the given point in the point cloud.

13. The system according to claim 12, wherein the programming instructions further comprise instructions to guide the sensor movement to a second location in the object based on an anatomy until a pre-defined criteria is met.

14. The system according to claim 13, wherein the predefined criteria comprises at least one of a number of iterations performed and a number of points in a cluster.

15. The system according to claim 12, wherein the programming instructions further comprise instructions to stop operations when a stop condition is met, where the stop condition is based on at least one of a Total Conduction Delay ("TCD") divided by a Cycle Length ("CL"), a Cycle Width ("CW") divided by CL, TCD/CW, patterns of previous mark locations on the grid, the source's distance from a current sensor location, and a source's distance from a previous sensor location.

16. The system according to claim 15, wherein the stop condition is selected based on at least one of an amplitude of the plurality of signals and a target type.

17. A system, comprising:
a processor; and
a non-transitory computer-readable storage medium comprising programming instructions that are configured to cause the processor to implement a method for guiding a sensor to a location of a propagating wave source, wherein the programming instructions comprise instructions to:
receive a plurality of signals generated by a plurality of electrodes of the sensor while the sensor resides at the first location in the object;
process the plurality of signals to determine coordinates of an estimated location of the propagating wave source relative to the first location at which the sensor resides; and
provide a visual aid facilitating sensor movement by plotting a mark on a grid overlaid on top of an object image displayed by the system;
wherein the plurality of signals are processed by:
using the plurality of signals to determine a Principle Wave Direction ("PWD") to the propagating wave source; and
using the PWD to determine if there are enough points to generate a point cloud.

18. The system according to claim 17, wherein the programming instructions further comprise instructions to guide the sensor to a next location in the object based on an anatomy if it is determined that there are not enough points to generate the point cloud.

19. The system according to claim 17, wherein the programming instructions further comprise instructions to generate the point cloud if it is determined that there are enough points to generate the point cloud.

20. The system according to claim 19, wherein the programming instructions further comprise instructions to group the points of the point cloud into at least one cluster.

21. The system according to claim 20, wherein the programming instructions further comprise instructions to use the point cloud and the at least one cluster to determine coordinates of the mark.

22. The system according to claim 21, wherein the coordinates are determined by:
identifying a cluster with a maximum density;
determining a weighted average of the identified cluster's points; and
performing a Bayesian filter algorithm using the weighted average to determine a next location in the object to where the sensor should be moved.

* * * * *